United States Patent [19]

Van Loveren et al.

[11] Patent Number: 4,614,299

[45] Date of Patent: * Sep. 30, 1986

[54] ARTICLE WHICH DISPENSES AT A CONSTANT RATE A VOLATILE COMPOSITION, AND PROCESS FOR USING SAME

[75] Inventors: Augustinus G. Van Loveren, Rye; Marina A. Munteanu, New York, both of N.Y.; Geoffrey B. Seaber, Ijsselstein, Netherlands

[73] Assignee: International Flavors & Fragrances Inc., New York, N.Y.

[*] Notice: The portion of the term of this patent subsequent to Jun. 14, 2000 has been disclaimed.

[21] Appl. No.: 620,085

[22] Filed: Jun. 13, 1984

[51] Int. Cl.$^4$ .......................... A61L 9/04; A61L 9/01; A61L 9/12
[52] U.S. Cl. ........................................ 239/6; 239/56; 239/60
[58] Field of Search .......................... 239/6, 34, 55–57, 239/60

[56] References Cited

U.S. PATENT DOCUMENTS

| | | | |
|---|---|---|---|
| 3,770,199 | 11/1973 | Hoek et al. | 239/54 |
| 3,844,865 | 10/1974 | Elton et al. | 156/229 |
| 3,870,593 | 3/1975 | Elton et al. | 161/159 |
| 3,885,737 | 5/1975 | Watkins | 239/34 |
| 4,014,501 | 3/1977 | Buckenmayer | 239/58 |
| 4,130,245 | 12/1978 | Bryson | 239/34 |
| 4,145,001 | 3/1979 | Weyenberg et al. | 239/56 |
| 4,161,283 | 7/1979 | Hyman | 239/55 |
| 4,226,944 | 10/1980 | Stone et al. | 239/60 |
| 4,227,024 | 7/1981 | Spector | 239/36 |
| 4,247,498 | 1/1981 | Castro | 264/28 |
| 4,248,380 | 2/1981 | Lee et al. | 239/53 X |
| 4,285,468 | 8/1981 | Hyman | 239/55 |
| 4,330,416 | 5/1982 | Sprecker | 252/8.9 |
| 4,387,849 | 6/1983 | Van Lovern et al. | 239/60 |
| 4,440,819 | 4/1984 | Rosser et al. | 428/273 X |
| 4,452,845 | 1/1984 | Lloyd et al. | 428/220 |

FOREIGN PATENT DOCUMENTS

| | | |
|---|---|---|
| 1922783 | 5/1984 | Australia . |
| 1021916 | 12/1977 | Canada . |
| 1039911 | 10/1978 | Canada . |
| 0046071 | 2/1982 | European Pat. Off. . |
| 0107915 | 9/1984 | European Pat. Off. . |
| 00326515 | of 0000 | Japan . |
| 5081655 | of 0000 | Japan . |
| 59-6059 | 1/1984 | Japan . |
| 1226841 | 3/1971 | United Kingdom . |
| 1414785 | 11/1975 | United Kingdom . |
| 2081721 | 2/1982 | United Kingdom . |

*Primary Examiner*—Andres Kashnikow
*Attorney, Agent, or Firm*—Arthur L. Liberman

[57] ABSTRACT

Described is an article which dispenses at a constant rate a volatile composition of matter into the atmosphere surrounding the article which volatile composition of matter can be, for example, a perfume composition or air freshener, which article is a container which is a hollow totally enclosed flexible, rigid or partially flexible-partially rigid structure comprising a thin shell totally enclosing an inner void, with the thin shell having a part thereof as a microporous polymer which contains a plurality of finite filler particles which that when the article is located in the ambient environment, the volatile material molecules are passed through the microporous polymer by means of an adsorption desorption mechanism or by means of capillary action. The volatile substrate which is a composition of matter is enabled to pass through the microporous polymer at a constant mass flow rate of both the individual volatile components and the total composition. Thus, the composition of matter passing through the microporous polymer remains unchanged insofar as its composition is concerned. The invention is enabled using a microporous polymer having the property of transporting water vapor at a rate of between 100 up to a 1000 g/m$^2$/day at about 25° C. and at about 50% relative humidity at about atmospheric pressure and having an air transport rate of 100–20,000 Gurley seconds (gs) and a thickness in the range of from about 0.01 mils up to about 20 mils.

12 Claims, 48 Drawing Figures

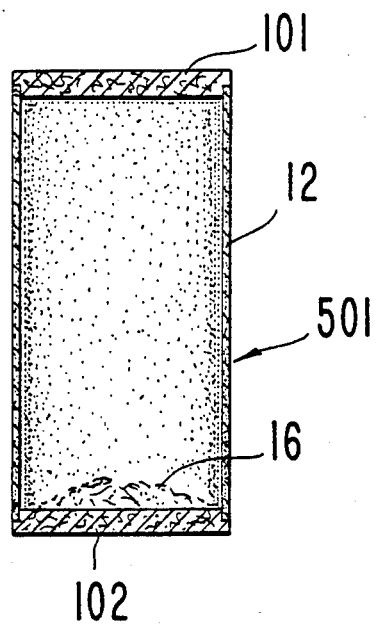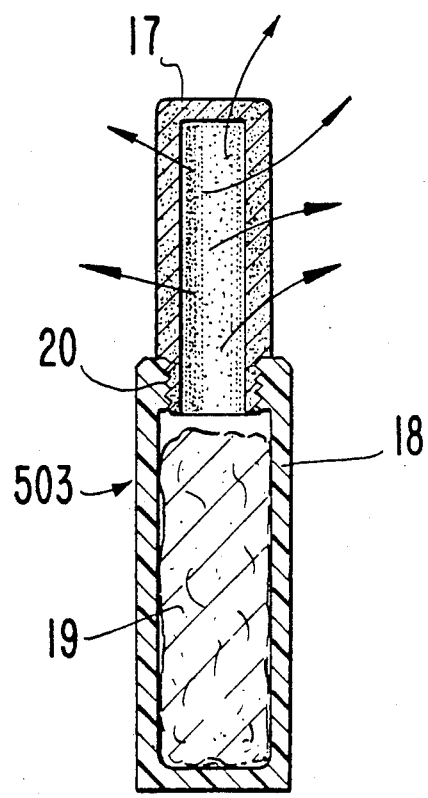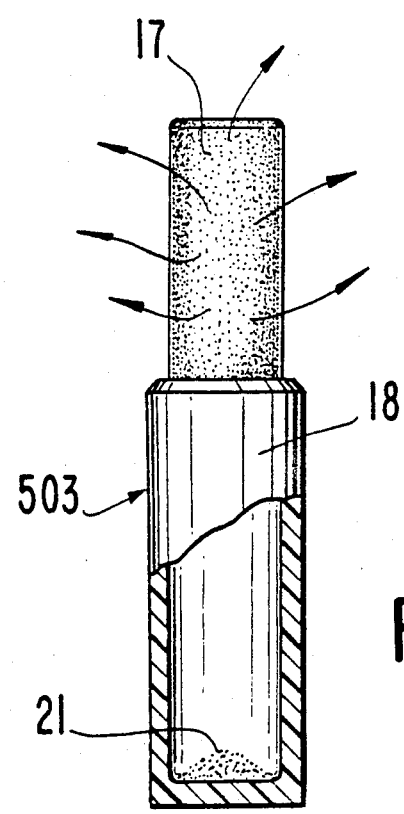

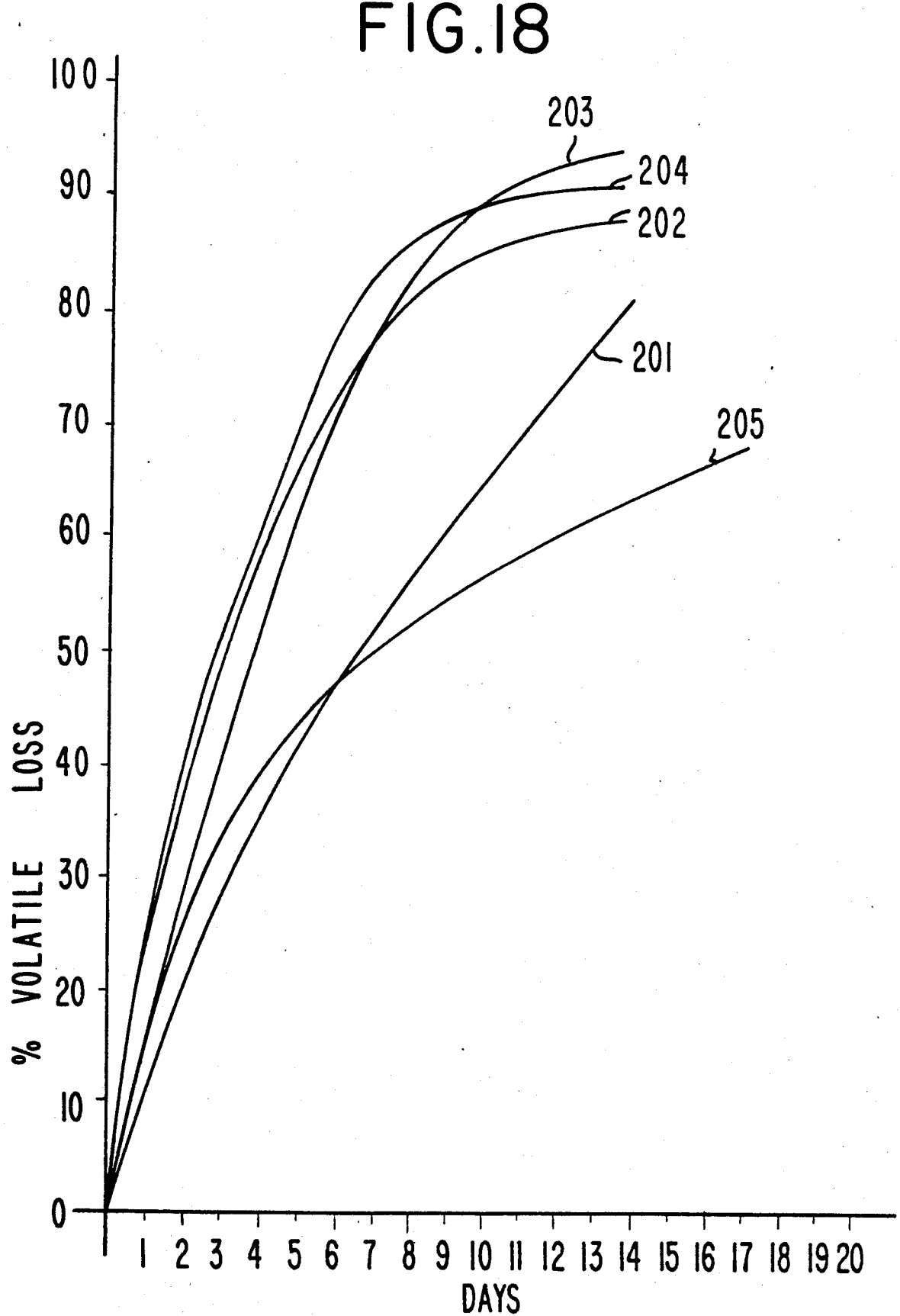

230
231

240
241

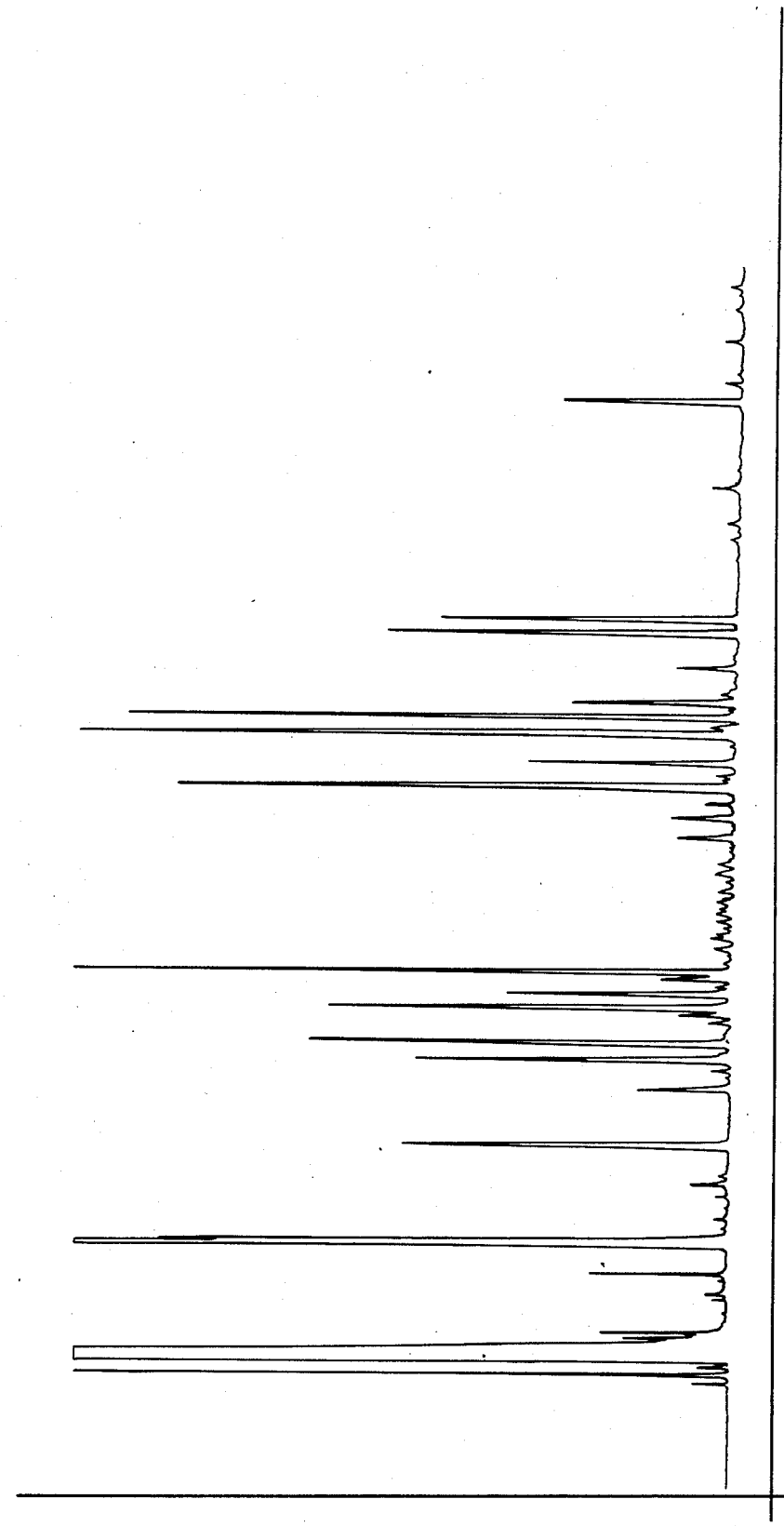
FIG.33 GLC PROFILE FOR EXAMPLE VI.

GLC PROFILE FOR EXAMPLE VI.

FIG.35 GLC PROFILE FOR EXAMPLE VI.

FIG. 37  GLC PROFILE FOR EXAMPLE VI

FIG. 38 GLC PROFILE FOR EXAMPLE VI.

GLC PROFILE FOR EXAMPLE VI

FIG.40 — GLC PROFILE FOR EXAMPLE VI

ARTICLE WHICH DISPENSES AT A CONSTANT RATE A VOLATILE COMPOSITION, AND PROCESS FOR USING SAME

BACKGROUND OF THE INVENTION

As a result of using a polymer shell or film or sheet, monolayer, bilayer, or multilayer, (hereinafter referred to as "membrane") that is defined by (i) having the property of either transporting water vapor at a rate of between about 50 up to about 1000 g/m²/day at about 25° C. and at about 50% relative humidity at about atmospheric pressure and/or having an air transport rate of 100–20,000 Gurley seconds (Gs) and (ii) a thickness in the range of from about 0.01 mils up to about 20 mils, our invention provides volatile substance-emitting apparatus and methods for producing same and for using same wherein the volatile substance can be an air freshener, standard aromatizing materials, odor maskants, insecticides, insect repellents, animal repellents, compositions for the evaluation of olfactory functioning in humans, herbicides, pheromones and the like. These volatile substances have previously been used with the following delivery systems:

aerosols;
gels;
paper;
felt;
large pore polymers;
powders;
candles; and
wick-containing liquids.

With the exception of aerosols, the concentration and rate of release of volatile substance, e.g., perfume, into the atmosphere surrounding the container or emitting apparatus has been a function of the rate of evaporation of volatile material which, in turn, has been a function of the remaining concentration of volatile material in the container or emitting apparatus. Accordingly, the rate of mass transfer (e.g., diffusion in certain instances) of the volatile substance into the surrounding atmosphere has, in the prior art, been "first order", that is, a function of the concentration previously present, e.g.:

$$(dc)/(dt) = kc$$

wherein c represents concentration of volatile material and k represents a constant.

Furthermore, with respect to the apparatus of the prior art there has been no practical way for ascertainment by the user as to whether or not the bulk of the volatile material has been depleted at a particular point in time. In all instances it is impossible to determine precisely when the volatile substance is no longer being discharged in an effective quantity and/or concentration per unit time into the atmosphere surrounding the container. In those situations where an aroma is being emitted, the actual aroma is usually relatively powerful during the emission notwithstanding the rate of emission of active agent and said aroma retains its power even after its practical effect (e.g., air freshening) is deminimis.

Thus, in Japanese Pat. No. J8-0036,515 assigned to Akane Soji K K, printings from which fragrance is gradually emitted are indicated to be produced by a process comprising (1) preparing fragrance-emitting ink compositions by dispersing (a) fragrance-emitting bases prepared by mixing perfume solutions with thermoplastic resins at elevated temperatures to homogenize the mixture, followed by cooling the mixture to separate fine particles of gelled resin in which the perfume is occluded in (b) a solution of film-forming material and (2) printing the base material with this fragrance-emitting ink composition.

Scent-releasing polyurethane foams are shown to be prepared in German published Application 2,945,757 (assigned to the Tenneco Chemical, Inc.). In published Application 2,945,757, it is indicated that a polyurethane foam containing a particulate filler and perfume is prepared by first mixing the filler with the perfume and adding this mixture to a liquid polyol and finally mixing the thus-obtained composition with an organic polyisocyanate, water and a catalyst to produce the resulting foam. It is indicated that the resulting material is used as an air freshener, deodorant, perfume sachet and the like. It is further indicated that the foam releases the perfume at a limited and constant rate. The said published German Application corresponds to U.S. Pat. No. 4,226,944 issued on Oct. 7, 1980.

U.S. Pat. No. 4,247,498 issued on Jan. 27, 1981 discloses a method for preparing a homogeneous microporous cellular polymer structure which evolves perfumes, insect repellents, odor masking agents and the like at a slow and steady rate. The process of U.S. Pat. No. 4,247,498 comprises (i) heating a mixture of a polymer which may be an olefinic polymer, condensation polymer, oxidation polymer or a blend thereof and a "compatible liquid" to a temperature and for a time sufficient to form a homogeneous solution, (ii) forming at substantially the same time a plurality of liquid droplets of substantially the same size in a continuous liquid polymer phase by cooling the solution, (iii) continuing cooling to solidify the polymer, (iv) then at least partially displacing the "compatible liquid" with a perfume, an odor masking agent, an insect repellant or the like. It is indicated at column 15, line 30 of U.S. Pat. No. 4,247,498 that the disclosed system may be used to create a "thin film of about 1 mil or less up to a relatively thick block of thickness of about 2⅜ inches".

Japanese published Application J5-5081,655 assigned to Kureha Chemical Industries KK discloses a slow release air aromatizing composition which comprises an aqueous solution of water soluble high molecular weight substance of viscosity 500–30,000 cps such as polyvinyl acetate, carboxymethyl cellulose, sodium alginate, xanthan gum, etc. admixed with an oil soluble perfume or a water soluble perfume.

U.S. Pat. No. 4,145,001 describes a package having plural layers with the quantity of volatile substance such as a deodorizer sandwiched between the layers. The outer layers of the laminate in U.S. Pat. No. 4,145,001 are impermeable to the substance and its vapors, and thus prevent the escape of vapors as long as the package is sealed. Upon opening of the package of U.S. Pat. No. 4,145,001, delamination occurs at the interface between two selected layers such that the volatile substance is covered on one side only by a layer of material which is permeable to the vapors, thereby allowing controlled release of the vapors over a period of time. A process for production of such package is also disclosed in U.S. Letters Pat. No. 4,145,001.

U.S. Pat. No. 4,161,283 issued on July 17, 1979 discloses an article for the slow release of volatilizable substances such as deodorizers, insecticides, repellents and the like, the article being formed from opposed outer and inner wall members joined along their peripheral portions to define a central reservoir portion for receiving and confining a volatile substance. The outer wall in U.S. Pat. No. 4,161,283 comprises a non-porous flexible polymeric sheet material which does not permit bulk flow but allows molecular diffusion therethrough. The inner wall member comprises an impermeable barrier layer. Another barrier layer is releasably bonded to the outer wall and prevents escape of volatilizable substance until its removal at the time of desired use. U.S. Pat. No. 4,285,468 issued on Aug. 25, 1981 discloses essentially the same subject matter as U.S. Pat. No. 4,161,283.

Nothing in the prior art, however, discloses the use of a polymeric membrane (shell, film, or sheet, monolayer, bilayer or multilayer) as defined by (i) having the property of either transporting water vapor at a rate of between about 50 up to about 1000 g/m$^2$/day at about 25° C. and at about 50% relative humidity at about atmospheric pressure and/or having an air transport rate of 100–20,000 Gurley seconds (Gs); and (ii) having a thickness in the range of from about 0.01 mils up to about 20 mils which gives rise to the novel structure and process for preparing same of our invention wherein a commercially viable structure capable of dispensing at a steady state and at a constant rate, either continuously or discontinuously for discrete periods of time, a volatile composition of matter such as perfume, air freshener, air deodorant or the like.

OBJECTS OF THE INVENTION

It is an object of our invention to provide a process for dispensing at an approximately constant rate, controllably, continuously or discontinuously, for discrete and controllable periods of time, volatilizable compositions of matter from a container into the environment surrounding such container.

It is a further object of our invention to provide a process for dispensing at an approximately constant rate, continuously or discontinuously for discrete and controllable periods of time volatile compositions of matter from a container into the atmosphere surrounding such container enabled by the use of a polymer shell or film or sheet, monolayer, bilayer or multilayer ("membrane") that is defined by (i) having the property of either transporting water vapor at a rate of between about 50 up to about 1000 g/m$^2$/day at about 25° C. and at about 50% relative humidity at about atmospheric pressure and/or having an air transport rate of 100–20,000 Gurley seconds (Gs); and (ii) a thickness in the range of from about 0.01 mils up to about 20 mils.

It is a further object of our invention to provide an apparatus useful for performing the process for dispensing at an approximately constant rate controllably, continuously or discontinuously for discrete periods of time such volatile compositions of matter.

It is a further object of our invention to provide a process for dispensing controllably, continuously or discontinuously for discrete periods of time at a constant rate, a perfume or air freshener or other volatile substance from a container into the environment surrounding said container so that when the effect of volatile composition of matter is depleted, the fact of actual depletion as well as the rate of depletion is easily determinable.

SUMMARY OF THE INVENTION

Our invention utilizes a polymer shell or film or sheet, monolayer, bilayer or multilayer (hereinafter referred to as "membrane") that is defined by having (i) the property of either water vapor at a rate of between about 50 up to about 1000 g/m$^2$/day at about 25° C. and at about 50% relative humidity at about atmospheric pressure and/or having an air transport rate of 100–20,000 Gurley seconds (Gs); and (ii) a thickness in the range of from about 0.01 mils up to about 20 mils, for enabling a process to take place for dispensing in a controllable manner at a constant rate, continuously or discontinuously for discrete periods of time at substantially stead state ("0 order") over an extended period of time a volatile composition of matter from a container into the environment surrounding the container. Our invention also defines an apparatus necessary and useful for carrying out this process. The apparatus includes a hollow totally enclosed structure comprising a thin shell totally enclosing an inner void, the thin shell having a base portion having an inner surface:

(i) contained totally within the inner void of the thin shell a volatile composition (which may optionally be temporarily entrapped in an entrapment material and totally entrapped in the entrapment material at least at the instant in time of commencement of the functional operation of the structure—that is, when it is removed from an air-tight package); and (ii) at least a finite section of said thin shell comprising a porous polymer that is defined by (i) the property of either transporting water vapor at a rate of between about 50 up to about 1000 g/m$^2$/day at about 25° C. and at about 50% relative humidity at about atmospheric pressure and/or having an air transport rate of 100–20,000 Gurley seconds (Gs); and (ii) a thickness in the range of from about 0.1 mils up to about 20 mils (e.g., a filled porous polymer containing embedded therein a plurality of finite solid particles) said porous polymer having a porosity such that when said hollow totally enclosed structure is located in an ambient environment said volatile material molecules are either (a) adsorbed onto the inner surface of the microporous polymer section and desorbed from the microporous polymer from the outer surface of the shell at a substantially constant mass flow rate both of the individual volatile components and totally flowing through such porous polymer section, or (b) transported through the porous polymer shell section by means of capillary action at a substantially constant mass flow rate both of the individual volatile components and totally flowing from said thin shell the driving force of such molecular transport resulting from a difference in concentration of volatile substance between:

(x) the gas phase of the inner void of said shell; and (y) the space immediately adjacent the outer surface of said microporous polymer shell section.

The microporous polymer shell section (also referred to herein as "lamina") useful in the practice of our invention has the following specifications:

(1) The property of transporting water vapor at a rate of between about 50 up to about 1000 g/m$^2$/day at about 25° C. and at about 50% relative humidity at about atmospheric pressure;

(ii) Porosity range: 100–20,000 Gurley seconds;

(iii) Most preferred porosity range: 8,000–12,000 Gurley seconds;

(iv) Range of Temperature for Operation: −80° C. up to 150° C.;

(v) Most preferred temperature range of Operation: 0° C.–60° C.; and (vi) A thickness in the range of from about 0.01 mils up to about 20 mils.

Certain statements concerning operation of the microporous polymer film ("membrane") of our invention are based upon information disclosed in the paper: PERMEATION OF PURE GASES UNDER PRESSURE THROUGH ASSYMETRIC POROUS MEMBRANES, MEMBRANE CHARACTERIZATION AND PREDICTION OF PERFORMANCE", Rangarajan, et al, *Ind.Eng.Chem.Proc.Des.Dev.*, 1984, 23, 79–87, the disclosure of which is incorporated herein by reference.

The term "polymer" in this case is intended to include polymers of varying molecular weights and degrees of branching, homopolymers, copolymers, terpolymers and the like, including but not limited to substances such as polyolefins (e.g., polypropylene), polyamides (e.g., nylon 66), polyfluorocarbons (e.g., TEFLON ®), polyesters, e.g. polyethylene terephthalate, polycarbonates, (e.g., LEXAN ®), polyacrylates, (e.g., LUCITE ®) and blends of same in various molar ratios.

The term "membrane" is intended herein to define porous polymeric shells, films or sheets, monolayer, bilayer or multilayer which on functional operation of the structure of our invention and thereafter, will have the ability to have transported therethrough volatile substances useful in the practice of our invention.

BRIEF DESCRIPTION OF THE DRAWINGS

FIG. 8 is an elevation view of the apparatus of FIG. 5 shown in cross section with the volatile substance previously contained in the cylindrical structure having been fully depleted.

FIG. 9 is an elevation view of another preferred embodiment of our invention, shown in cross section with the volatile substance contained in the structure of our invention being fully loaded in said structure immediately prior to use.

FIG. 10 is an elevation view of the structure of FIG. 9 shown in cross section with the entrapped volatile substance previously contained in said structure having been fully spent.

FIG. 18 is a series of graphs of *percent volatiles lost versus time* comparing the functional use of structures as illustrated in FIG. 1 containing temporarily-entrapped volatilizable substance (air freshener), not containing volatilizable substance (but replaced by ethanol, per se) and standard commercial air fresheners of the prior art as defined according to U.S. Pat. No. 4,014,501. The graphs are more particularly described in Examples I and II(A), infra.

FIG. 21 indicates three separate use (followed by storage) periods for the structure of FIG. 6.

FIG. 33 is a GLC profile of the fragrance material denoted as "278 m" employed in Example VI at time, t=0 weeks.

DETAILED DESCRIPTION OF THE INVENTION

Figure 1:
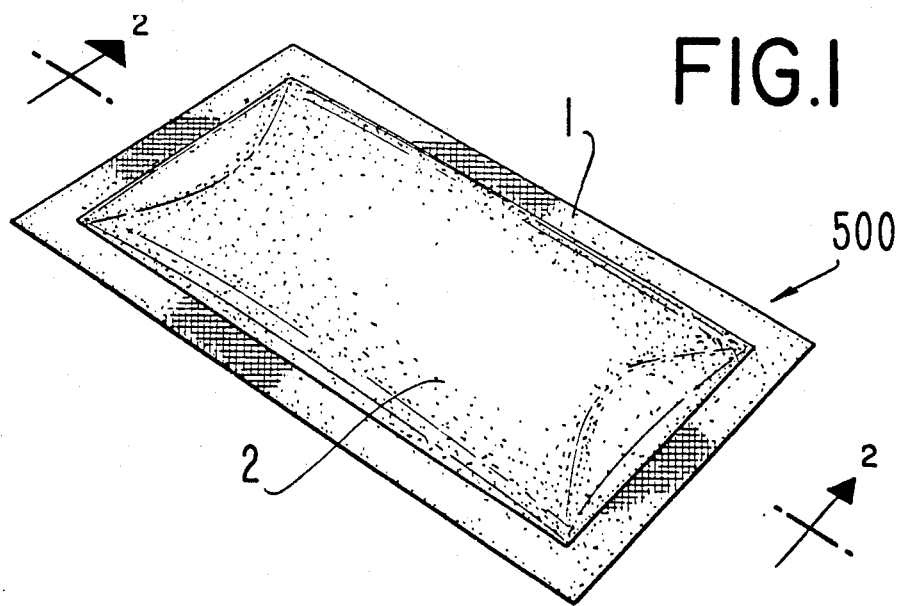
FIG. 1 is a perspective view of a preferred embodiment of the hollow totally enclosed structure of our invention, with the material of fabrication being flexible polypropylene film.
Figure 2:
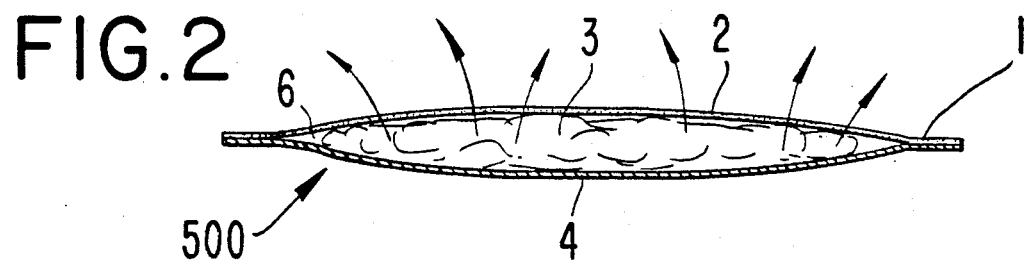
FIG. 2 is a cut-away elevation view of the hollow totally enclosed structure of FIG. 1 shown in cross section with the structure fully loaded with temporarily-entrapped volatile substance.
Figure 20:
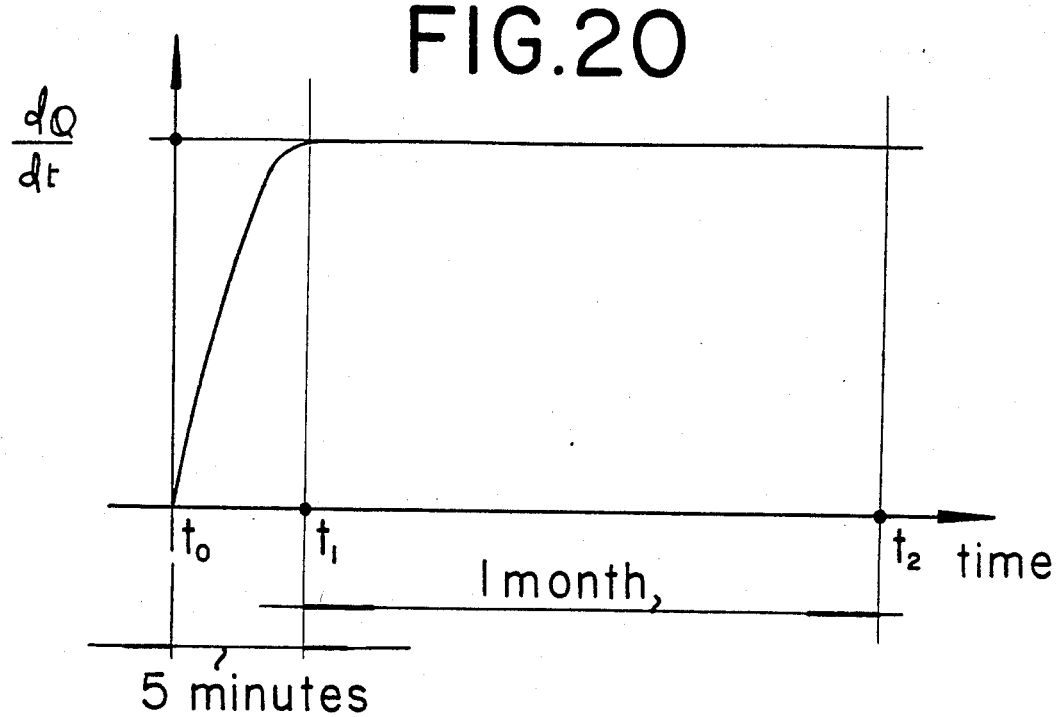
FIG. 20 represents a graph of rate of fragrance loss versus time for the structure of FIG. 1 for up to one month of use.

The process of our invention comprises dispensing continuously (as illustrated in FIG. 20) or discontinuously for discrete periods of time (as shown in FIG. 2) at steady state, a volatile composition of matter 3 from a container, e.g., as represented by reference numeral "500" in FIG. 1, into the atmosphere surrounding said container enabled by the use of a polymeric membrane that is defined by having (i) the property of either transporting water vapor at a rate of between about 50 up to about 1000 g/m²/day at about 25° C. and at about 50% relative humidity at about atmospheric pressure and/or having an air transport rate of 100–20,000 Gurley seconds (Gs) and (ii) having a thickness in the range of from about 0.01 mils up to about 20 mils.

The steps of this process are exemplified using the structure 500 as follows:

(a) providing, and, optionally, entrapping a volatile composition of matter which may be a perfume composition, an air freshening composition, a deodorizing composition, an animal repellent composition, an insect repellent composition, an insecticide, a herbicide or a pheromone composition or the like, in an entrapment agent whereby a temporarily entrapped volatile composition 3 is formed;

(b) providing a first thin shell section 4 composed of a thin polymeric shell having a curved surface and having an inner void portion, an inner surface and an outer surface and having a first sealable continuous circumferential edge and a first geometric configuration;

(c) placing the volatile composition or entrapped volatile composition 3 in the inner void portion of the first thin shell section and onto the inner surface of the first thin shell section 4;

(d) providing a second thin shell section 2 having a second sealable circumferential edge and a shape and volume which are such that when said second circumferential edge is placed in conforming adjacent edgewise contact with said first sealable circumferential edge, a totally enclosed shell structure 500 is produced with said entrapped volatile composition 3 being totally enclosed within said shell structure leaving a void 6 between said second thin shell section 2 and said volatile substance 3;

(e) placing said second thin shell section 2 having a second sealable continuous circumferential edge which substantially conforms in shape to said first sealable circumferential edge onto said first thin shell section 4 whereby said first sealable edge is in closely fitting sealable proximity with said second sealable edge at location 1;

(f) sealing said first sealable edge to said second sealable edge at location 1 with at least a finite section of preferably the second thin shell section being a microporous polymer having a porosity such that when the hollow totally enclosed structure, now sealed, 500 is located in the ambient environment said volatile material molecules are transported by means of capillary action and/or adsorption/desorption mechanisms at a substantially constant mass flow rate both of the individual volatile components and totally through said microporous polymer section;

(g) optionally, at time intervals of non-use, or for storage purposes, placing the entire shell structure 500 into an outer container 7 which may or may not be transparent and sealing the opening of the outer container at 8 whereby the outer container 7 is air-tight. The outer container 7 prevents the escape of the volatile substance from the entrapment medium into the atmosphere prior to the desired operation of the shell structure and during storage thereof. The outer container 7 has a volume greater than the shell structure which is the functional portion of the apparatus of our invention. The outer container may or may not be transparent or it may be partially transparent.

An example of the aforesaid porous polymer composition of matter is as follows:

A microporous film containing filler having the following specification:

| | |
|---|---|
| Composition | Polypropylene + CaCO₃ filler |
| Thickness | 100 micrometers |
| Weight | 90 g/m² |
| Ultimate tensile strength | 30 MN/m² (machine direction) |
| | 11 MN/m² (transverse direction) |
| Elongation at break | 180% (machine direction) |
| | 350% (transverse direction) |
| Pore size | 0.2 micrometers (max.) |
| Void volume | 0.34 cm³/g (30%) |
| Density | 900 kg/m² |
| Air flow | 3 cm³/cm²/min at 1 kg/cm² |
| Water flow | 0.001 cm³/cm²/min at 1 kg/cm² |
| Air resistance (Gurley) | 10,000 secs. |
| Water vapour transmission | 150 g/m²/24 hrs. at 23° C. and 50% relative humidity |
| Thermal stability | 10 hrs. at 130° C. | wherein MN is meganewtons, m is meters, g is grams, and cm is centimeters. Additional examples are those where the air resistance (Gurley) varies from about 8000 seconds up to about 12,000 seconds.

The microporous polymer membrane section useful in the practice of our invention has the following specifications:

(i) Water vapor transmission rate: from about 50 g/m²/day up to about 100 g/m²/day at about 25° C. and at about 50% relative humidity at about atmospheric pressure;

(ii) Porosity range: 100–20,000 Gurley seconds;

(iii) Most preferred porosity range: 8,000–12,000 Gurley seconds;

(iv) Range of Temperature for Operation: from −80° C. up to +150° C.;

(v) Most preferred temperature range of operation: from 0° C. up to 60° C.; and (vi) A thickness in the range of from about 0.01 mils up to about 20 mils.

The statements concerning operation of the microporous polymer membrane of our invention are based upon information disclosed in the paper: "PERMEATION OF PURE GASES UNDER PRESSURE THROUGH ASSYMETRIC POROUS MEMBRANES, MEMBRANE CHARACTERIZATION AND PREDICTION OF PERFORMANCE", Rangarajan, et al *Ind. Eng. Chem. Proc. Des. Dev.*, 1984, 23, 79–87, the disclosure of which is incorporated by reference herein.

Rangarajan, et al hypothesizes that one of the following five mechanisms are operative in working with the microporous polymeric membrane as used herein, to wit:

(i) Molecular diffusion (following Fick's Law);
(ii) Capillary:
   (a) Knudsen Flow;
   (b) Slip Flow; and
   (c) Viscous Flow;
(iii) Adsorption/Desorption.

We show herein that the probability of mechanism (i) contributing in any substantial manner to the operation of our invention is negligible.

Although a filler is not required insofar as the microporous polymeric membrane useful in our invention is concerned, it is now preferred that a filler be incorporated therein having an average particle size of from about 0.1 up to about 20 micrometers.

Particulate or pulverulent fillers which are useful in the practice of this invention include, but are not limited to, clays, including both untreated clays and those which have been surface-treated in various ways well known in the art, ground limestone, talc, precipitated calcium carbonate, including surface-treated types, alumina, aluminium silicate, barytes, wollastonite or other calcium silicate, silica, zirconia, titanium dioxide, and polymeric fillers such as pulverized phenolic resins, polyamides, (e.g., nylon 66), polyfluorocarbons, (e.g., TEFLON ®), polyesters, e.g., polyethylene terephthalate, polycarbonates, (e.g., LEXAN ®) polyacrylates, (e.g., LUCITE ®).

The only limitations are that the fillers should not adversely affect or react with the aromatizing or other functional volatile substance or any entrapping material which may be used in entrapping the aromatizing or other functional volatile substance, or absorb the aromatizing or other functional volatile material to such a degree that release from the microporous polymer membrane is unduly inhibited or entirely prevented. Although the particle size of the filler can be varied over a wide range, e.g., 0.1 micrometers up to 20 micrometers, extremely coarse particles are generally undesirable because they may detract from the physical functioning and mechanical operability of the membrane which is the key functioning member of the apparatus of our invention, as well as the aesthetic qualities of the finished microporous polymeric membrane.

The amount of filler can be varied over a wide range depending on the amount of volatilizing material to be released from the entrapped volatilizable substance 3 and the vapor viscosity of the volatile vapor being transported (which is either transported by means of capillary action and/or is adsorbed onto and desorbed from the porous polymer). We have found that filler levels in a range of from 5 to 100 parts by weight per 100 parts of polymer are generally satisfactory, although greater or lesser amounts can be used if desired. Indeed, it is not necessary to use any filler so long as the polymeric menbrane has (i) the property of either transporting water vapor at a rate of from about 50 $g/m^2/day$ up to about 1000 $g/m^2/day$ at about 25° C. and at about 50% relative humidity at about atmospheric pressure and/or having an air transport rate of 100–20,000 Gurley seconds (Gs) and (ii) a thickness in the range of from about 0.01 mils up to about 20 mils.

Any type of volatile substance transported, e.g., perfume composition can be used in the practice of this invention provided that it does not react with any component of the microporous polymer or other substance used in fabricating the outer shell of the structure of our invention. Fragrances are usually complex mixtures and no component of the desired fragrance should be reactive with any component of the microporous polymer or any other component which is used to fabricate the shell structure of our invention.

Figure 4:
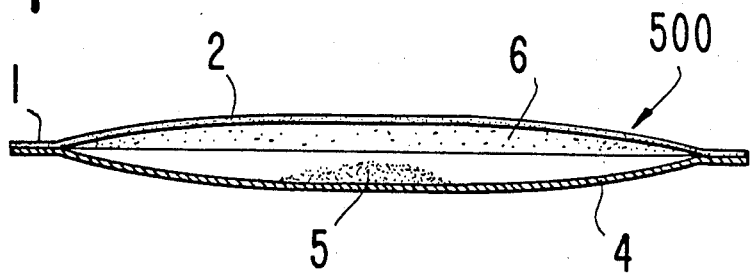
FIG. 4 is an elevation view of the structure of FIG. 1 shown in cross section with the volatile substance completely spent.

When the structure of our invention is ready to be used in dispensing at a substantially steady state and constant rate and continuously or discontinuously for discrete periods of time from container 500, the container 500 is removed from outer container 7 and maintained in any convenient area or 3-space. FIG. 4 illustrates the container 500 in cross section after the entrapped volatile material is totally depleted as a result of the substantially steady state mass transport of the volatile substance through microporous polymer section of a portion of the container wall, e.g., preferably wall 2. The fully depleted substance is shown in FIG. 4 as indicated in reference numeral "5".

If desired, as an additional embodiment of this invention, each of the shell structure of our invention may be interconnected as shown in FIGS. 11, 12, 13, 14, 15, 16 and 17 as structures 504, 505 and 506. Thus, a plurality of hollow totally enclosed structures, having upper portions 23A, 23B, 23C, 23D, 23E, 23F, 23G, 23H and 23J are laterally and detachably interconnected, having a common midplane 22A, each of said structures being connected to at lease two other of said structures, for example in structure 504, at a location midway between the base portion of each of said structures and the upper portion of each of said structures, with the base portion and upper portion of three of said interconnected structures shown in FIG. 12, to wit: the upper portions as 23C, 23D and 23J and the lower portions shown as 29C, 29D and 29J.

In constructing such a structure as structure 504 in FIGS. 11, 12, 13, 14, 15, 16 and 17, the upper polymeric portion containing upper portions 23A, 23B, 23C, 23D, 23E, 23F, 23G, 23H and 23J having a sealable circumferential edge 22A is sealed to a diametrically opposed lower portion containing such lower portions as 29C, 29D and 29J at sealable circumferential edge 22B with sealable circumferential edges 22A and 22B being in closely fitting sealable proximity with one another whereby when they are sealed, an air-tight connection is produced with the only means of ingress and egress from the voids 27C, 27D and 27G for the volatile substances contained in 26C, 26D and 26J being through microporous polymer sections in upper shell portions 23C, 23D, 23J and the like, and/or lower portions 29C, 29D and 29J and the like.

Necessarily, the volatile substance which would be contained in a gel must not come in direct liquid-solid phase contact with the microporous polymer membrane 23A, 23B, 23C, 23D, 23E, 23F, 23G, 23H and 23J. In order to avoid such a situation, an interposing mesh of much greater porosity than that of the microporous polymer membrane is made part of the construction, e.g., 126J, 126B, 126C, 127J, 127D and 127C and the like. The use of this interposing polymeric mesh may be constructed of polypropylene, for example, and it will enable the creation of embodiments of this invention such as those illustrated in FIGS. 11, 12, 13, 14, 15 and 16.

Figure 13:
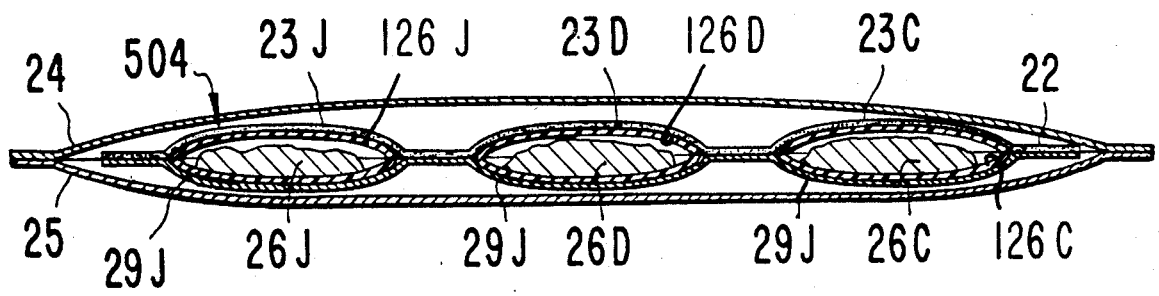
FIG. 13 is an elevation view of the apparatus of FIG. 11 shown in cross section with each of the inter-connected structures of the structure of FIG. 11 fully loaded with volatile substance prior to use, the plurality of inter-connected structures being contained in an air-tight sealed enclosure structure which has a volume greater than the volume of the plurality of inter-connected sealed structures.
Figure 14:
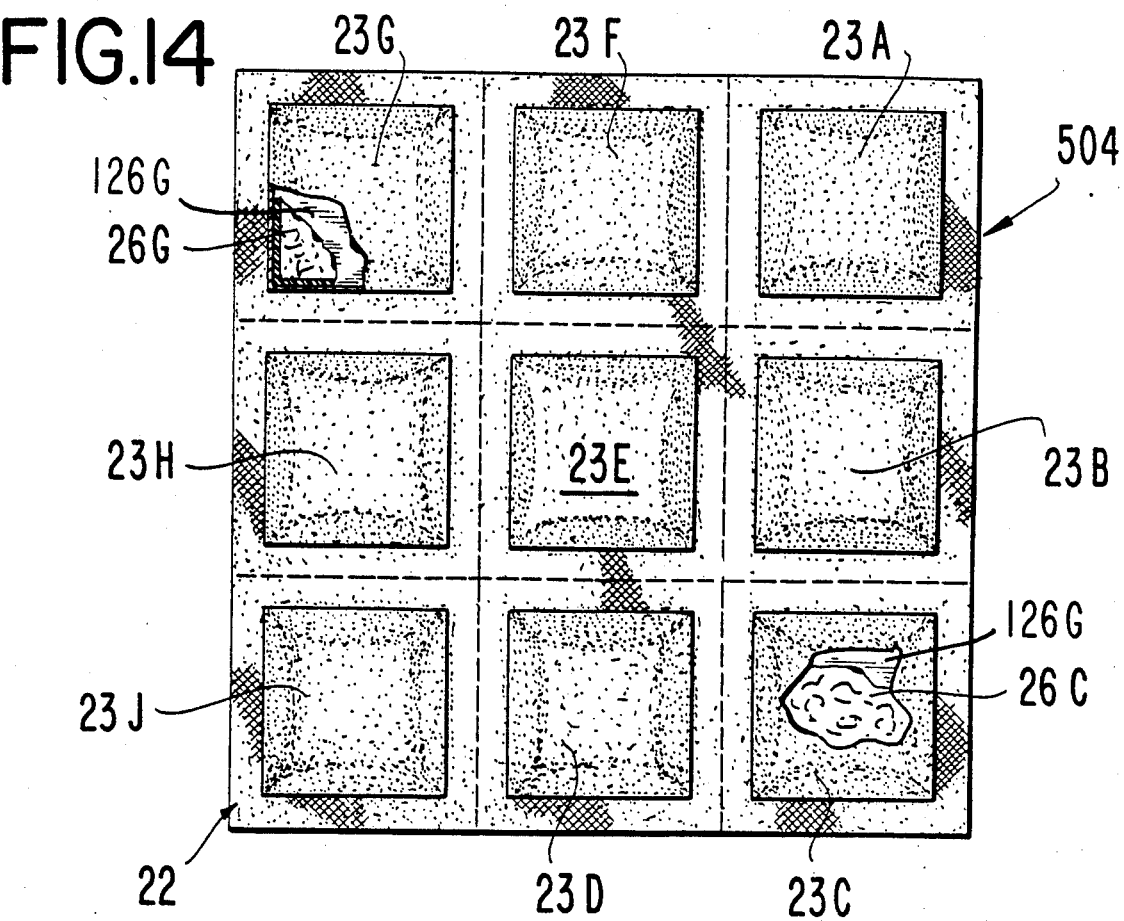
FIG. 14 is a plan view of the plurality of inter-connected structures of FIG. 11.
Figure 15:
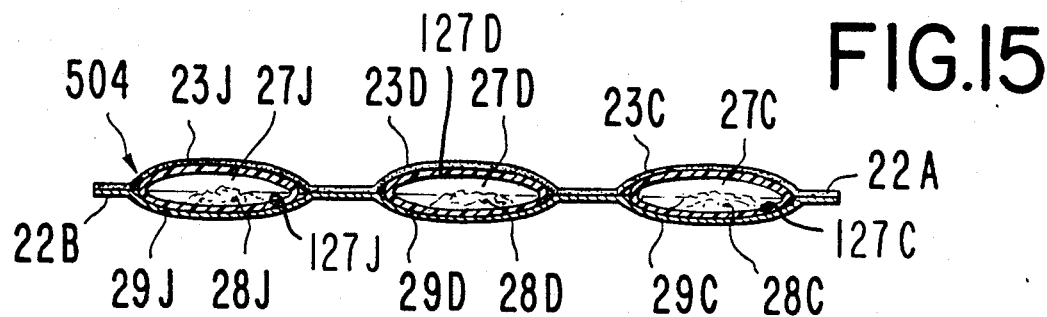
FIG. 15 is an elevation view of the structure of FIG. 11 which is actually a plurality of inter-connected structures (as the individual structure of FIG. 1), with each of the individual structures containing spent volatile substances immediately subsequent to the last functional use of said structure.
Figure 16:
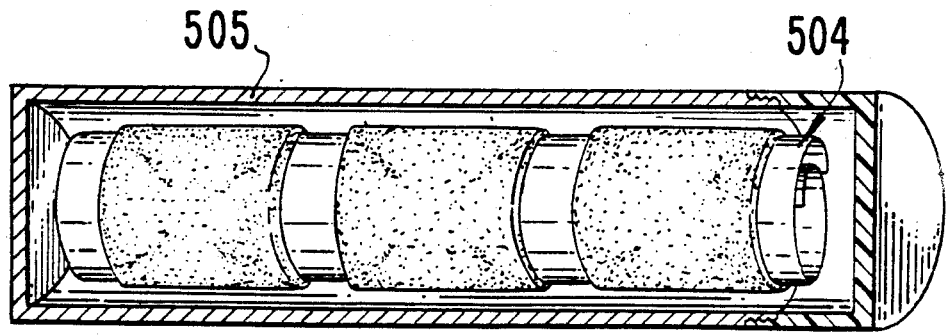
FIG. 16 is a perspective cross-sectional view of the structure of FIG. 11 rolled up and placed in an air-tight cylindrical outer-container when not being used.

Thus, when such a structure as structure 504 as illustrated in FIGS. 11, 12, 13, 14 and 15 are produced, they must be stored while not in use in a container such as container 24 as illustrated in cross section in FIG. 13 or they may be rolled up and stored in container 505 as illustrated in FIG. 16. Conveniently, the container 505 in FIG. 16 is cylindrical in shape and has a closure which is in the form of a screw top which may be easily removed and replaced for the purposes of storing structure 504 while not in use. When structure 504 is stored while not in use, the pressure within container 505 and without structure 504 and within structure 504 is equalized so that during storage no mass transfer from such entrapped volatile substance material as 26C, 26D and 26J takes place into the outer atmosphere.

After the structure 504 is removed from the outer container such as container 24 or container 505, it is then placed in an appropriately convenient place and the volatile substance is depleted from such substances as 26C, 26D and 26J until such point as the substance is totally depleted as illustrated in FIG. 16 (as reference numerals 28C, 28D and 28J).

Figure 17:
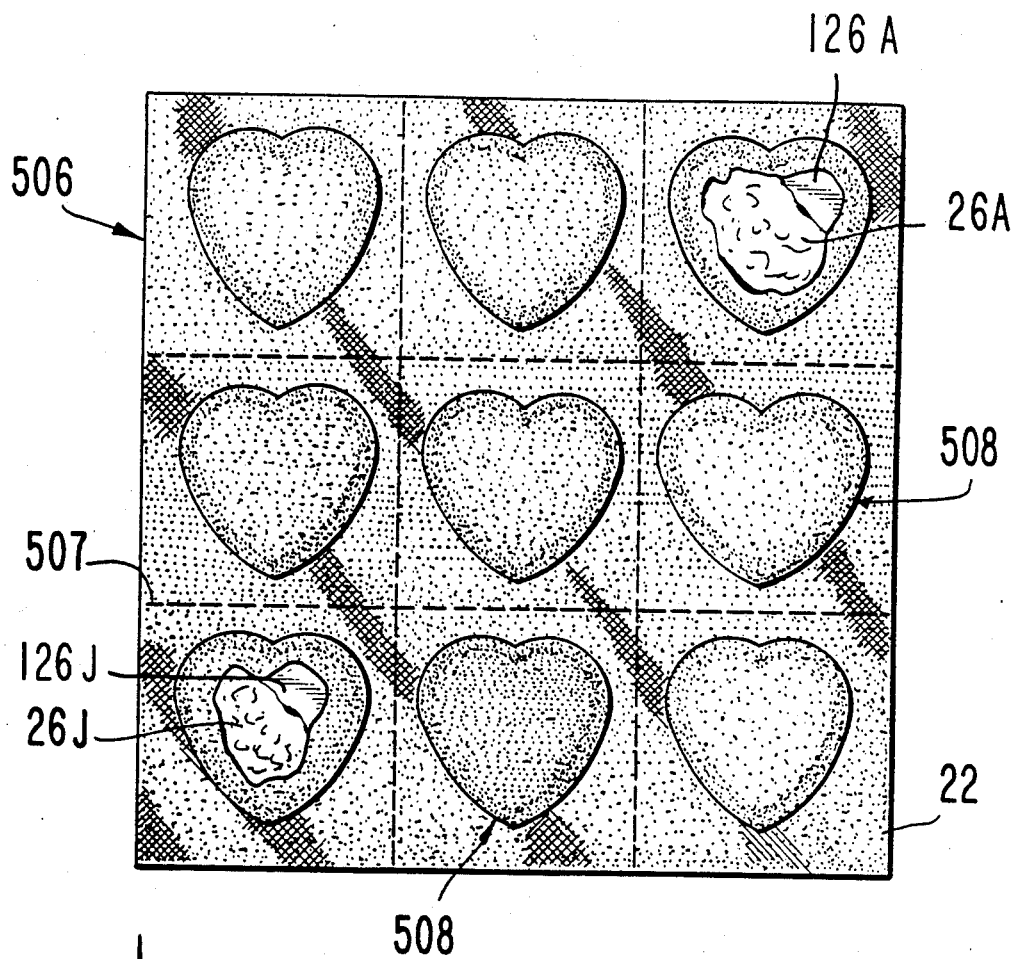
FIG. 17 is a perspective view of another preferred embodiment of our invention wherein a plurality of hollow totally enclosed structures are laterally and detachably inter-connected and have a common midplane with each of said structures being connected to at least two other of said structures at a location midway between the base portion of each of said structures and the upper portion of each of said structures and along at least a portion of the circumferential sealed edges of each of said structures sealing said upper portions of said base portions. In the embodiment as set forth in FIG. 17, the shape of the individual structures is "heart"-shaped rather than ellipsoidal in shape.

FIG. 17 illustrates a variation of structure 504 as structure 506 wherein the individual structures may be separated for individual use at 507, with the shape of the upper portion of each of the individual structures indicated as a "heart" shape at 508.

Comparative operation of structure 500 with perfumed fragrance entrapped material or ethyl alcohol entrapped material at 3 with material 3 in prior art apparatus (e.g., that described in U.S. Pat. No. 4,014,501) is set forth in FIG. 18. The graphs shown by reference numerals 201 and 203 represent the operation of structure 500 (percent volatile substance loss versus time) without any perfume material contained within the entrapped volatile substance 3 but only containing ethyl alcohol entrapped in gel 3. The graphs shown by reference numerals 202 and 204 (percent perfume lost versus time) indicate the *rate of release versus time* using structure 500 when employing 2% fragrance in a gel indicated by reference numeral 3. The microporous polymer used in structure 500 has the following specifications:

| Composition | Polypropylene + CaCO$_3$ filler |
|---|---|
| Thickness | 100 micrometers |
| Weight | 90 g/m$^2$ |
| Ultimate tensile strength | 30 MN/m$^2$ (machine direction) |
| | 11 MN/m$^2$ (transverse direction) |
| Elongation at break | 180% (machine direction) |
| | 350% (transverse direction) |
| Pore size | 0.2 micrometers (max.) |
| Void volume | 0.34 cm$^3$/g (30%) |
| Density | 900 kg/m$^3$ |
| Air flow | 3 cm$^3$/cm$^2$/min at 1 kg/cm$^2$ |
| Water flow | 0.001 cm$^3$/cm$^2$/min at 1 kg/cm$^2$ |
| Air resistance (Gurley) | 10,000 secs. |
| Water vapour transmission | 150 g/m$^2$/24 hrs. at 23° C. and 50% relative humidity |
| Thermal stability | 10 hrs. at 130° C. | as manufactured by Koninklijke Emballage Industrie Van Leer B.V. of Amstelveen, The Netherlands.

In each of the graphs wherein perfumed material is used, it is apparent that for the major portion of the useful life of the structure, e.g., structure 500, the rate of mass transport of perfume substance, when in use, is "0" order, that is:

$$(dg)/(dt) = k$$

wherein k is a constant and q is measure of the output of volatile substance for the outer surface of the outer polymeric membrane of the article of our invention.

Discussion covering the preparation of the compositions of matter which constitute the fragranced gels and unfragranced gels whereby the graphs as represented by reference numerals 201, 202, 203, 204 and 205 of FIG. 18 are prepared is set forth in Examples I and II, infra.

Figure 19:
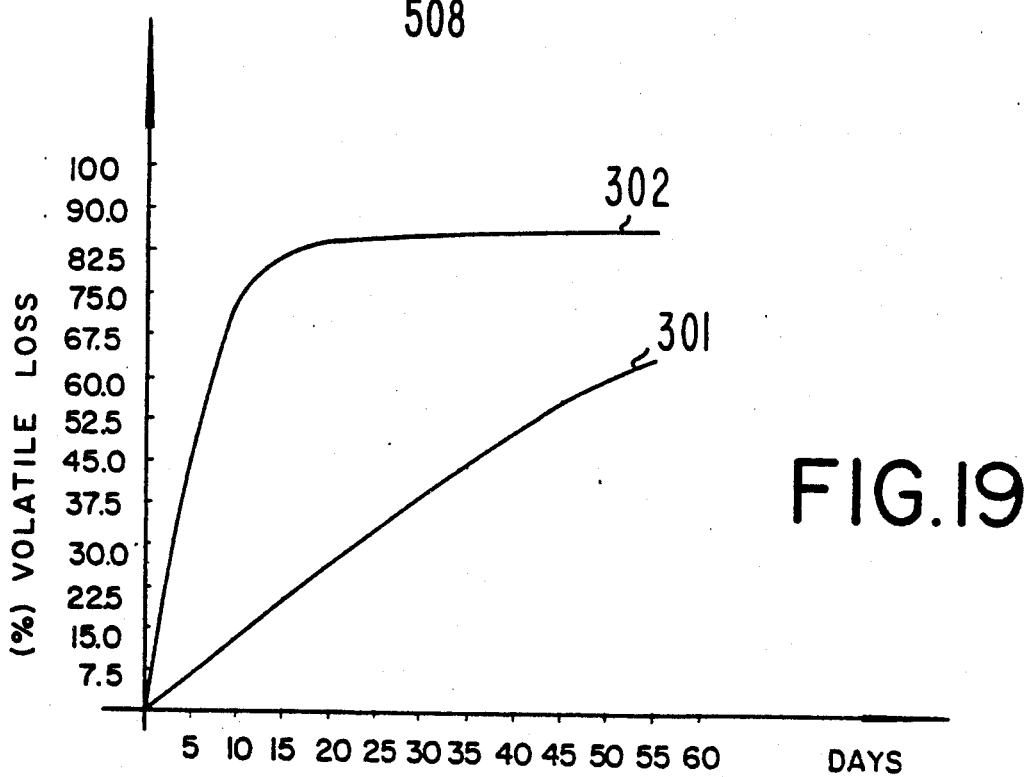
FIG. 19 is a comparative graph showing *percent fragrance loss versus time* for a structure containing air freshener-containing volatilizable substance as set forth in FIG. 1 versus the same volatilizable substance (air freshener contained in a gel) in the absence of said structure of our invention. (The graph is more particularly described in Example II(B), infra.)

By the same token, in FIG. 19, the graph indicated by reference numeral "302" indicates percent fragrance loss versus time for a fragrancing gel containing 2% by weight fragrance but *not* enclosed in a structure defined according to our invention. It will be noted that the diffusion of perfume compositions or other volatile substances as stated hereinbefore is in accordance with the ordinary diffusion laws and is not steady state, to wit:

$$(dg)/(dt) \neq \text{Constant}$$

Figure 3:
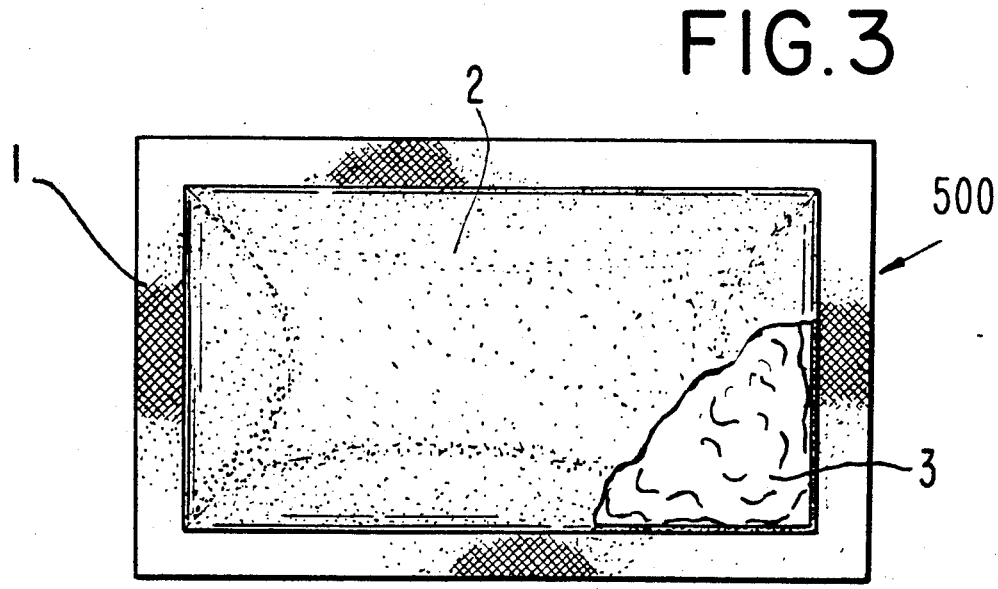
FIG. 3 is a partial cut-away plan view of the structure of FIG. 1 with the structure fully loaded with volatile substance immediately prior to functional use thereof.

On the other hand, the graph indicated by reference numeral "301" in FIG. 19 is for the same air freshener gel 3 containing 2% by weight fragrance (as more particularly described in Example III) located in the thin shell structure of our invention as illustrated in FIGS. 1, 2 and 3. The depleted air freshener gel is shown by reference numeral 5 in FIG. 4 (the depletion being at the end of a 55 day period as shown on the graph indicated by reference numeral "301" in FIG. 19).

Figure 42:
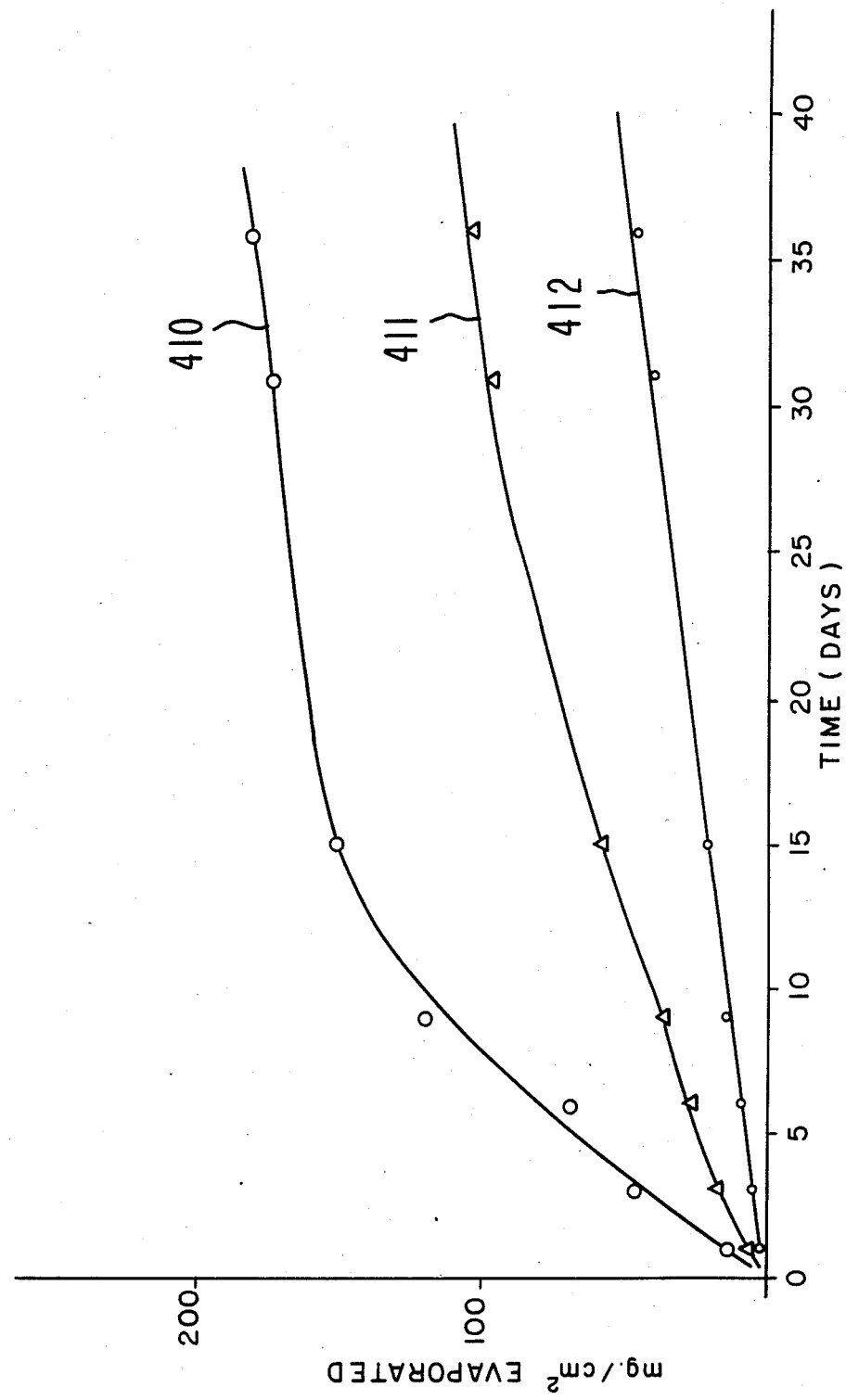
FIG. 42 represents a series of graphs indicating mg/cm$^2$ evaporated of fragrance through the membranes; a filled polypropylene membrane (reference numeral "411") and a nonfilled polypropylene membrane (reference numeral "412") and in addition, shows evaporation without the use of any membrane (reference numeral "410") as specifically set forth in detail in Example III, infra wherein the data points are set forth in tabular form.
Figure 43:
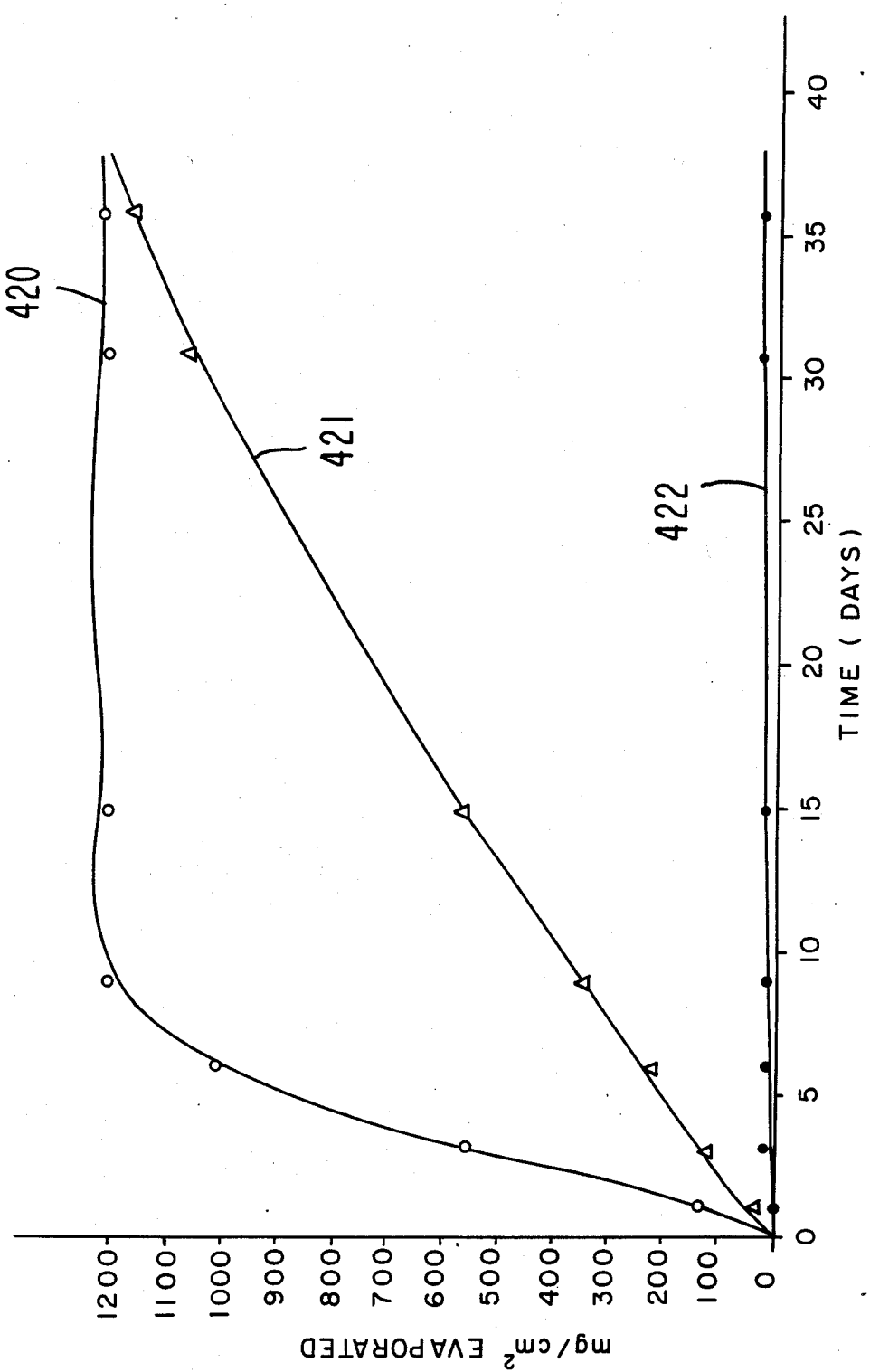
FIG. 43 is another series of graphs showing evaporation in mg/cm$^2$ vs. time in days for fragrance which is a 2% mixture of fragrance in Carbopol gel as specifically exemplified in Example III. The graph indicated by reference numeral "420" is a graph for evaporation without any interference from a membrane. The graph indicated by reference numeral "421" is the graph showing rate of evaporation through a membrane which is filled polypropylene and is a membrane defined according to our invention. The graph indicated by reference numeral "422" is the graph for evaporation through a polypropylene membrane, not defined within the parameters of our invention.

Discussion covering the preparation of the compositions of matter which constitute the fragrances and fragranced gels whereby the graphs as represented by reference numerals "410", "411" and "412" in FIG. 42 and reference numerals "420", "421" and "422" in FIG. 43 are prepared as set forth in Example III, infra.

The graph indicated by reference numeral "410" in FIG. 42 indicates mg/cm$^2$ evaporated of fragrance where the fragrance is *not* enclosed in a structure defined according to our invention. The graph indicated by reference numeral "411" in FIG. 42 is for the same fragrance (indicated as "EGL-1433") (as more particularly described in Example III) located in the thin shell structure of our invention as illustrated in FIGS. 1, 2, 3 and 5. The graph indicated by reference numeral "412" indicates percent fragrance loss (mg/cm$^2$) vs. time for the same fragrance (EGL-1433) located in a thin shell structure wherein the membrane, rather than being a membrane as defined for use with our invention [(i) having the property of either transporting vapor at a rate of between about 50 g/m$^2$/day up to about 1000 g/m$^2$/day at about 25° C. and at about 50% relative humidity at about at atmospheric pressure and/or having an air transport rate of 100–20,000 Gurley seconds (Gs) and (ii a thickness in the range of from about 0.01 mils up to about 20 mils] uses a polypropylene membrane which has properties including a water transport property outside of the range of the properties of the membranes useful in our invention.

In FIG. 43, the graph indicated by reference numeral "420" indicates fragrance loss (in mg/cm$^2$ evaporated) vs. time for an air freshener gel containing 2% by weight fragrance but *not* enclosed in a structure defined according to our invention.

The graph indicated by reference numeral "421" is for the same fragrance gel containing 2% by weight fragrance (as more particularly described in Example III) located in the thin shell structure of our invention as illustrated in FIGS. 1, 2 and 3.

The graph indicated by reference numeral "422" in FIG. 43 is for the same fragrance gel containing 2% by weight fragrance (as more particularly described in Example III) located in a thin shell structure of our invention as indicated in FIGS. 1, 2 and 3 wherein the membrane of the structure of our invention is replaced by a polypropylene membrane having an infinite resistance (as being essentially non-porous).

Figure 21:
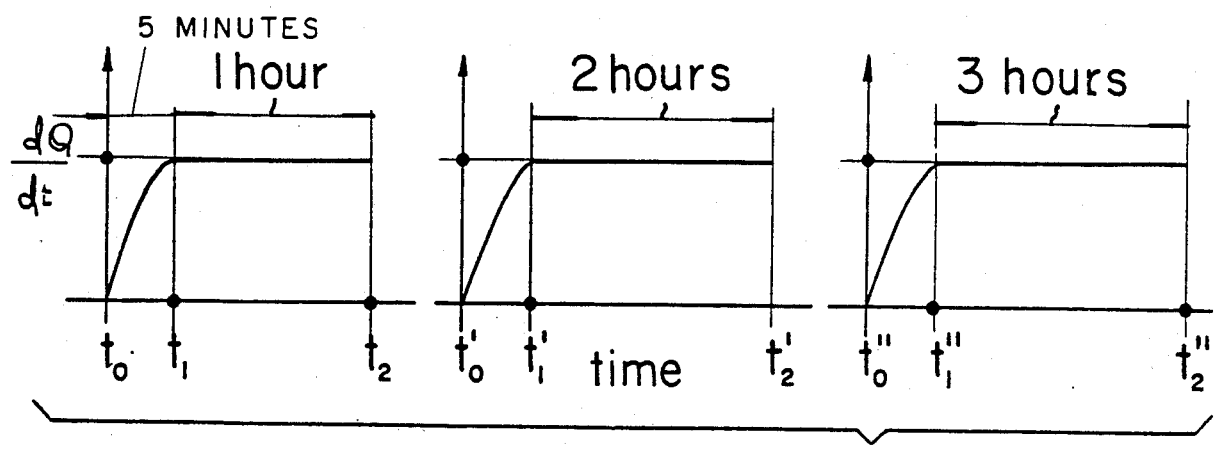
FIG. 21 represents an operational graph of rate of fragrance loss versus time for a structure as shown in FIG. 6 wherein the structure of our invention is removed from an outer container for operation and then replaced in the outer container when not in use and the outer container is resealed when not in use.

FIGS. 20 and 21 show, respectively, continuous and discrete usages of the shell structure as illustrated in FIG. 1. FIG. 20 is a graph of (dq)/(dt) versus time; wherein during the first five minutes of operation, the mass transfer rate is described as "*unsteady state*" until a "steady state" condition is reached wherein (dq)/(dt) is a constant for at least one month (until depletion as shown in FIGS. 4 and 8).

Figure 7:
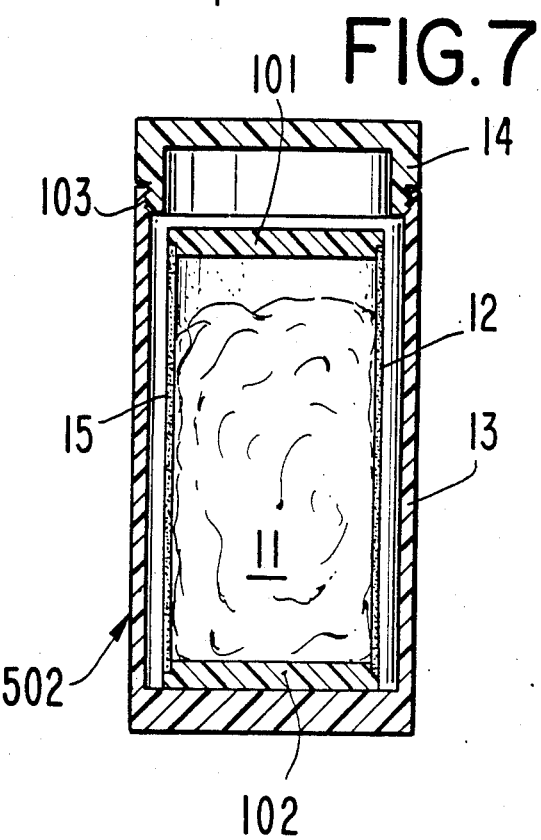
FIG. 7 is an elevation view of the cylindrical apparatus of FIG. 5 shown in cross section, with the volatile substance being fully loaded in said structure of FIG. 5, the structure of FIG. 5 contained in a larger enclosing cylinder which is air-tight whereby the structure of FIG. 5 is not in functional use.
Figure 6:
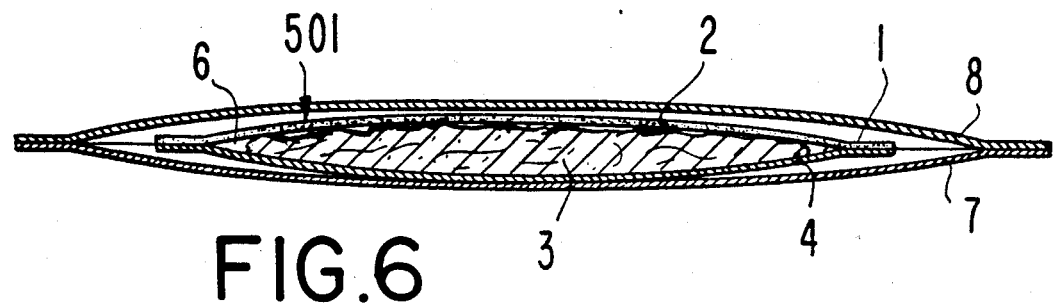
FIG. 6 is an elevation view of the apparatus of FIG. 1 shown in cross section fully loaded with volatile substance immediately prior to functional use thereof, the structure being located within an outer larger air-tight structure, the apparatus containing the entrapped volatile substance not being in functional use.
Figure 11:
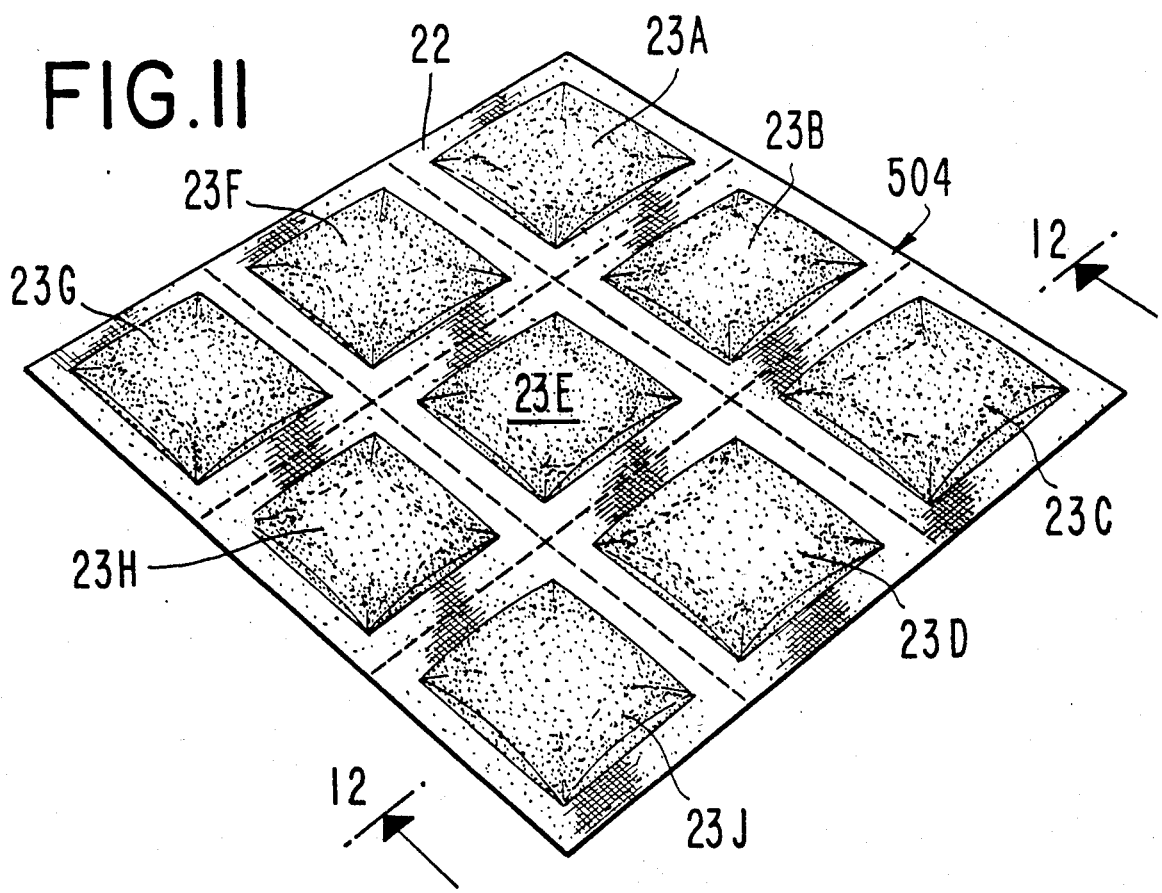
FIG. 11 is a perspective view of a structure in accordance with our invention where multiple structures (as the individual structure of FIG. 1) are connected to one-another at locations midway between the base portions of each of said structures and the upper portions of each of said structures and along at least portions of the circumferential sealed edges of each of said structures which are sealing the upper portion of each of said structures to the base portion of each of said structures.
Figure 12:
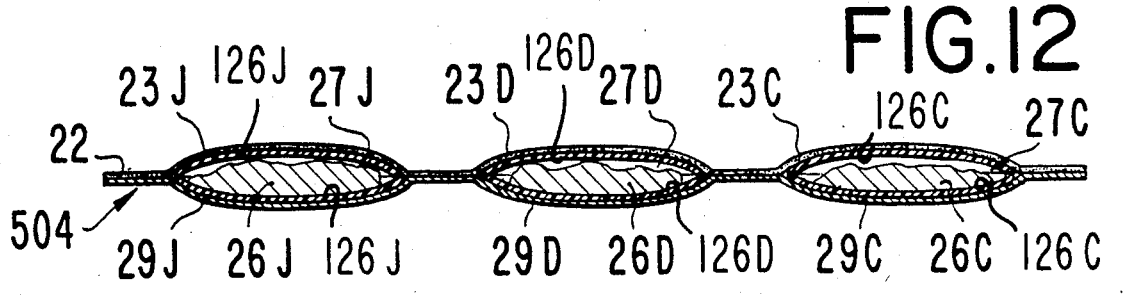
FIG. 12 is an elevation view of the structure of FIG. 11 shown in cross section with each of the individual structures of the inter-connected plurality of structures being fully loaded with volatile substance immediately prior to functional use thereof.

In FIG. 21, (dq)/(dt) is a constant after the first five minutes of usage until the time that the shell structure of our invention as shown in FIG. 1 is placed into an outer container as shown in any one of FIGS. 6, 7 or 16.

Figure 22:
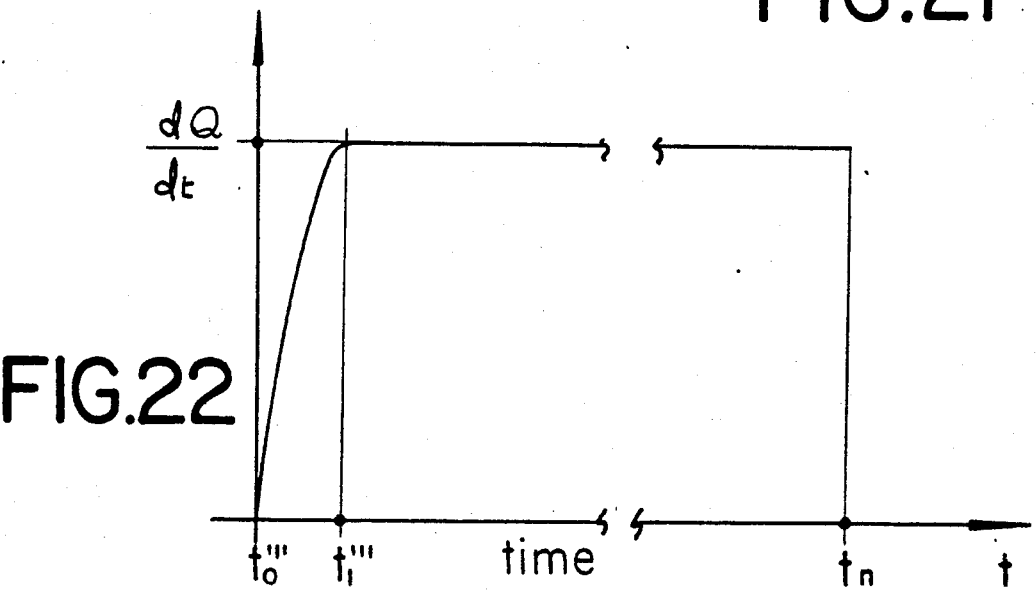
FIG. 22A represents a graph of rate of fragrance loss (dq/dt) versus time (resulting from a "time lag effect") for the entire period of possible continuous use of the structure of FIG. 1 assuming that the structure of FIG. 1 is not replaced at discrete time intervals in an enclosed air-tight outer container.
FIG. 22B represents a graph of rate of fragrance loss (dq/dt) versus time (resulting from a "burst effect") for the entire period of possible continuous use of the structure of FIG. 1 assuming that the structure of FIG. 1 is not replaced at discrete time intervals in an enclosed air-tight outer container.
FIG. 22C represents graphs of fragrance loss versus time in the case of a "burst effect" (B) and in the case of a "lag effect" (L).

FIG. 22A is a graph of (dq)/(dt) versus time (resulting from a "time lag effect") wherein the period of from $t_0'''$ to $t_1'''$ is a condition of "unsteady state" mass transport (usually no more than a few minutes) and the period from $t_1'''$ to $t_\omega$ is a condition of "steady state" mass transport; a very long period of time, e.g., 55–75 days and even longer.

Figure 22B:
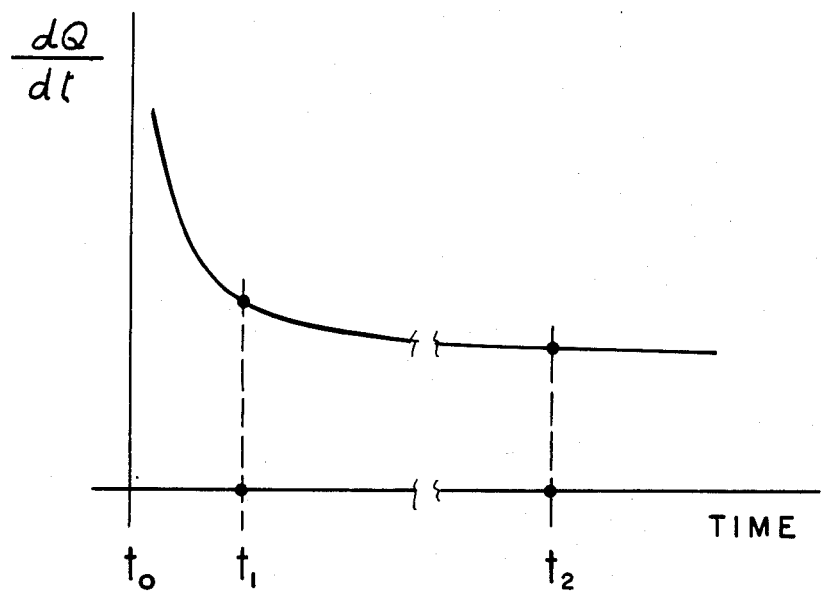

FIG. 22B is a graph of (dq)/(dt) versus time (resulting from a "time burst" effect after a buildup of fragrance within the totally enclosed structure of our invention) wherein the period of from $t_0$ to $t_1$ is a condition of "unsteady state" mass transport (usually no more than a few minutes) and the period from $t_1$ to $t_2$ is a condition of "steady state" mass transport; a very long period of time, e.g., 55–75 days and even longer.

Figure 22C:
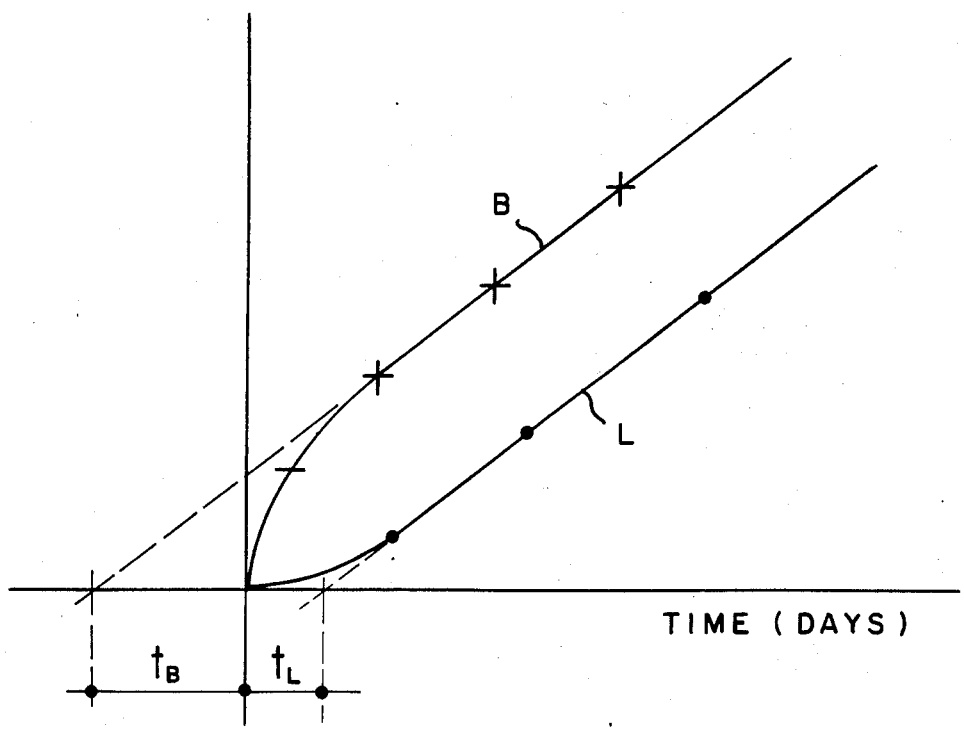

FIG. 22C shows graphs of fragrance loss versus time in the case of a "burst effect" (graph "B") and in the case of a "lag effect" (graph "L"). Reference: Robinson "Sustained And Controlled Release Drug Delivery Systems" published by Marcel Dekker Inc. (1978), pages 258 and 259.

Figure 23:
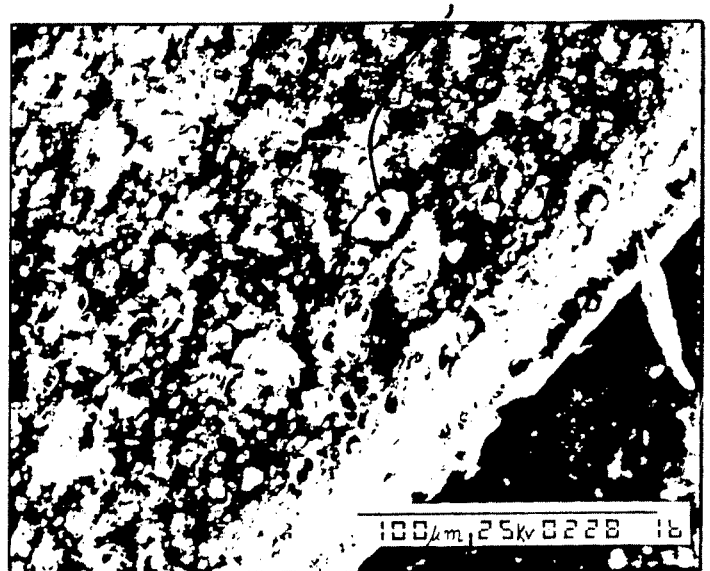
FIG. 23 represents a random section of a filled porous polymer lamina (12,000 Gurley second film) magnification of 500×, using a scanning electron miscroscope, which filled porous polymer lamina is useful in the practice of our invention.
Figure 24:
FIG. 24 represents a random section of a filled porous polymer lamina, (12,000 Gurley second film) magnification of 3500×, using a scanning electron microscope, which filled porous polymer lamina is useful in the practice of our invention.

FIGS. 23 and 24 set forth scanning electron microscope photographs of porous polymer film filled with $CaCO_3$ filler. FIG. 23 is a photograph showing 500× magnification. FIG. 24 is a photograph showing 3500× magnification.

Figure 25:
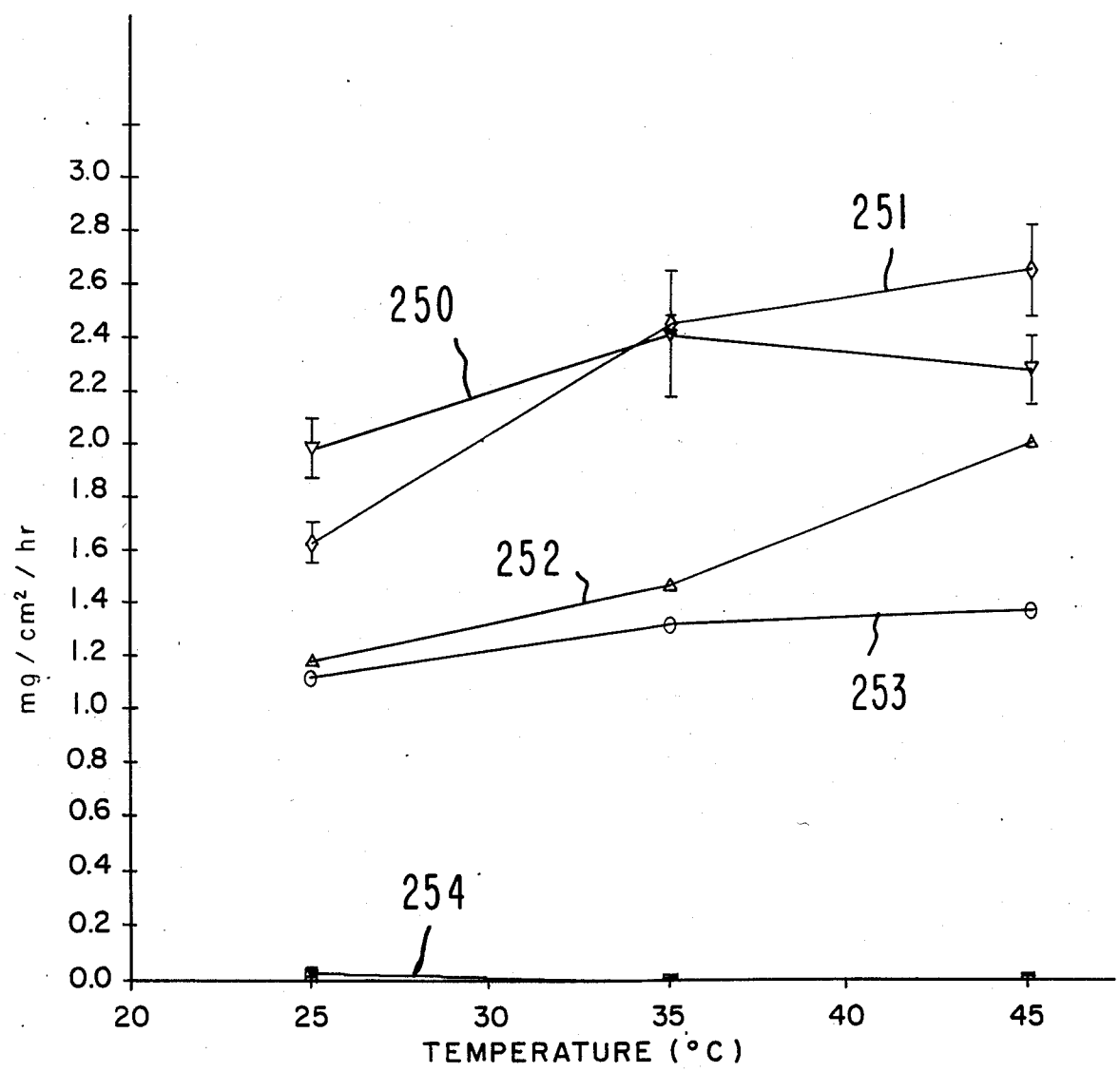
FIG. 25 is a plot of transport rate (of water vapor) versus temperature through filled porous polypropylene films of the nature exemplified herein, infra.

In FIG. 25, (which is a plot of transport rate of water vapor versus temperature in degrees centigrade), the graph indicated by reference numeral "250" is a graph of transport rate versus temperature for film having a porosity of, nominally, 8000 Gurley seconds.

The graph indicated by reference numeral "251" is a graph of transport rate versus temperature for water loss from a silanized 8000 Gurley second film (the silanization being carried out by treatment with a trimethylchlorosilane silanizing agent).

The graph indicated by reference numeral "253" in FIG. 25 is a graph of transport rate versus temperature in degrees centigrade for rate of water loss from a nominally 12,000 Gurley second filled polypropylene film.

The graph indicated by reference numeral "252" in FIG. 25 shows transport rate versus temperature in degrees centigrade for rate of water loss from a silanized nominally 12,000 Gurley second film.

The graph indicated by reference numeral "254" is a graph of transport rate versus temperature in degrees centigrade for rate of water loss from an untreated non-porous non-filled polypropylene film.

Both treated and untreated films as depicted in the graphs in FIG. 25 were placed into diffusion cells as illustrated in FIGS. 29–32, inclusive which were loaded with distilled water. The cells were then placed in a constant temperature/humidity oven at 25° C. and 63.5% relative humidity. These conditions provided for a nominal water vapor differential of 10 Torr between the inside and the outside of the cells. After two days, the temperature was adjusted to 35° C. and the relative humidity to 79% providing the same nominal 10 Torr water vapor pressure differential.

The graph indicated by reference numeral "253" in FIG. 25 is a graph of transport rate versus temperature in degrees centigrade for rate of water loss from a nominally 12,000 Gurley second filled polypropylene film.

The graph indicated by reference numeral "254" is a graph of transport rate versus temperature in degrees centigrade for rate of water loss from a non-porous, non-filled polypropylene film.

The films as depicted in the graphs in FIG. 25 were placed into diffusion cells as illustrated in FIGS. 29–32 which were loaded with distilled water. The cells were then placed in a constant temperature/humidity oven at 25° C. and 63.5% relative humidity. These conditions provided for a nominal water vapor differential of 10 Torr between the inside and the outside of the cells. After two days, the temperature was adjusted to 35° C. and the relative humidity to 79% providing the same nominal 10 Torr water vapor pressure differential.

Figure 29:
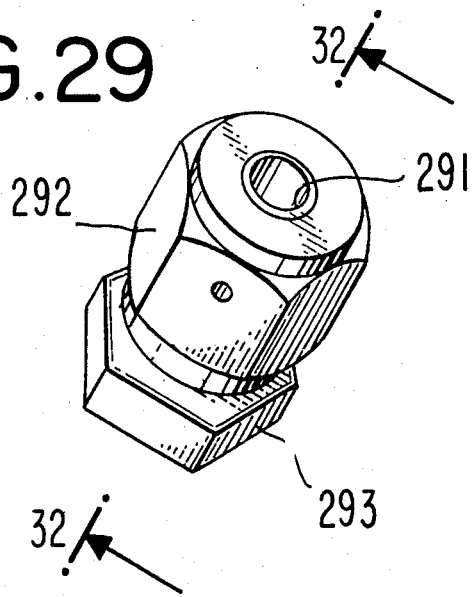
FIG. 29 is a perspective view of a cell used for determining the data as presented in the graphs of FIGS. 25, 26A, 26B, 26C, 27A, 27B and 28.
Figure 31:
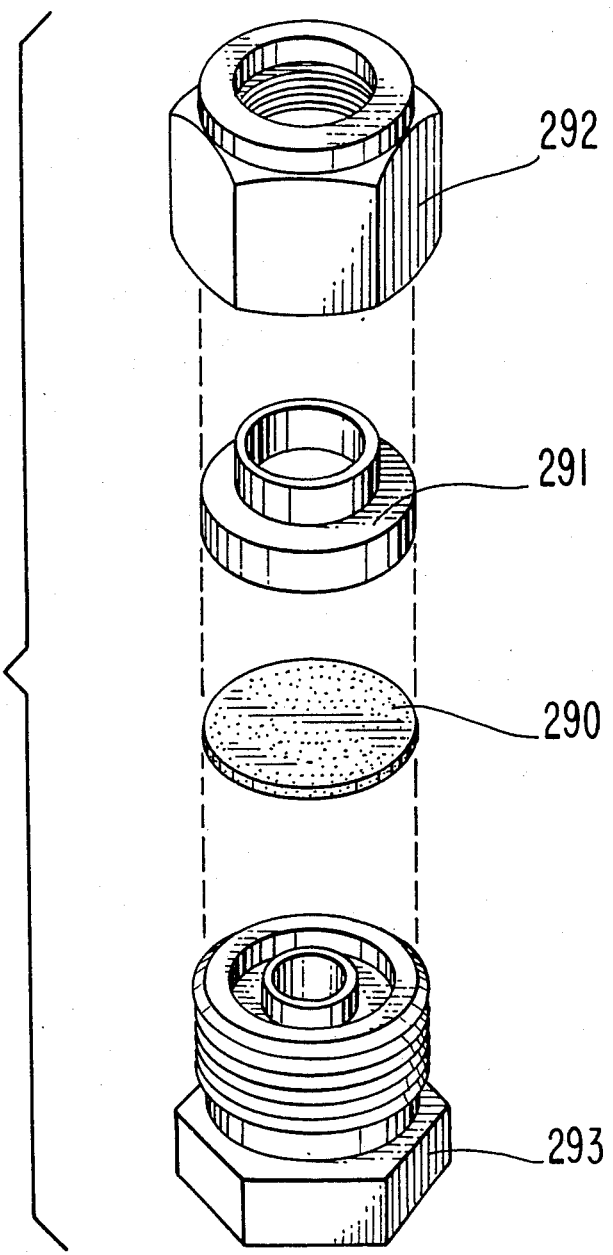
FIG. 31 represents an "explosion" of the parts of the cell of FIG. 29 and is indicative of how these parts are put together in order to enable the cell to be used to determine the data presented in the graphs of FIGS. 25, 26A, 26B, 26C, 27A, 27B and 28, inclusive.
Figure 34:
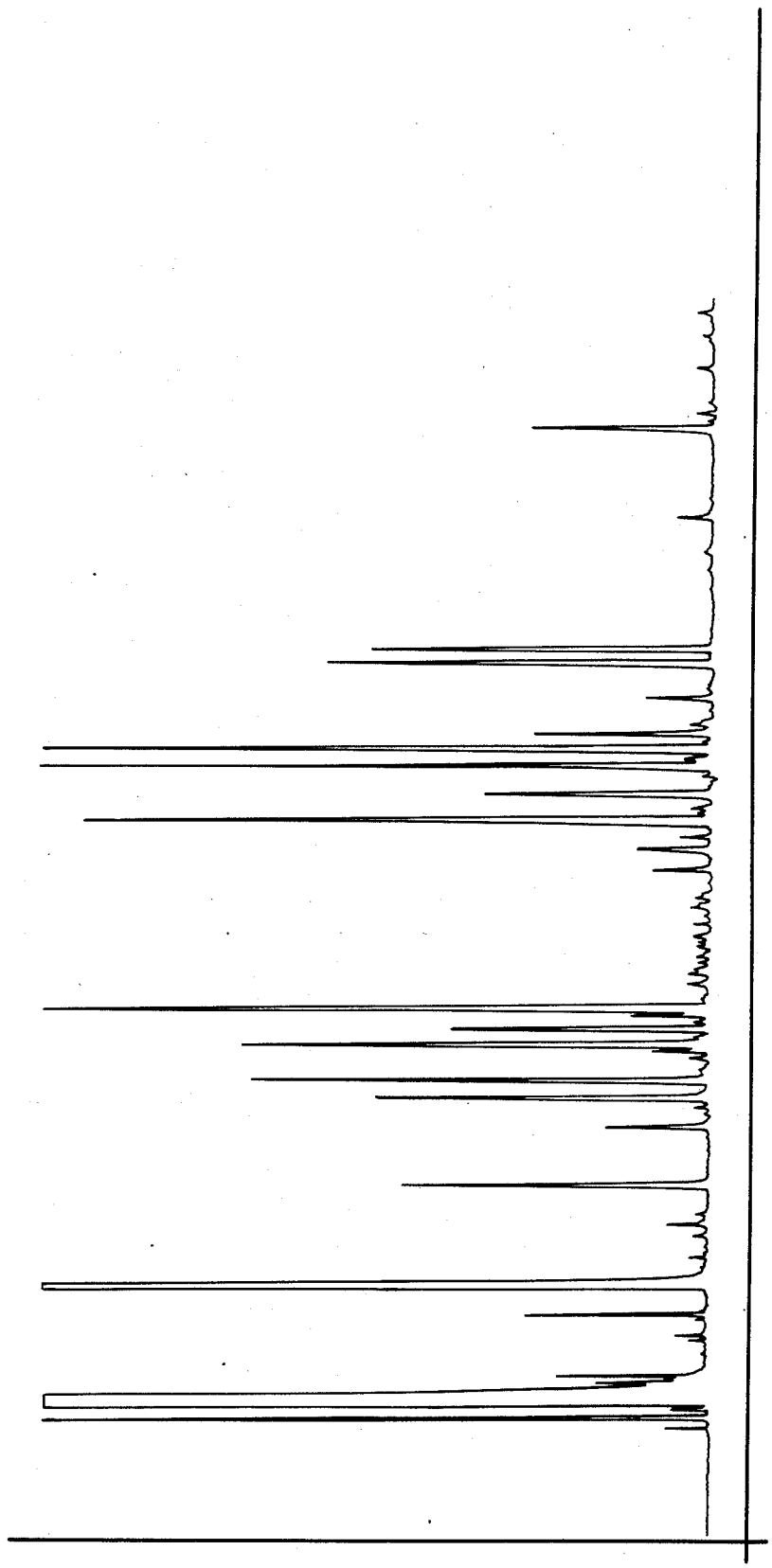
FIG. 34 is a GLC profile for perfume composition "278 m" employed in Example VI at t=2 weeks.
Figure 35:
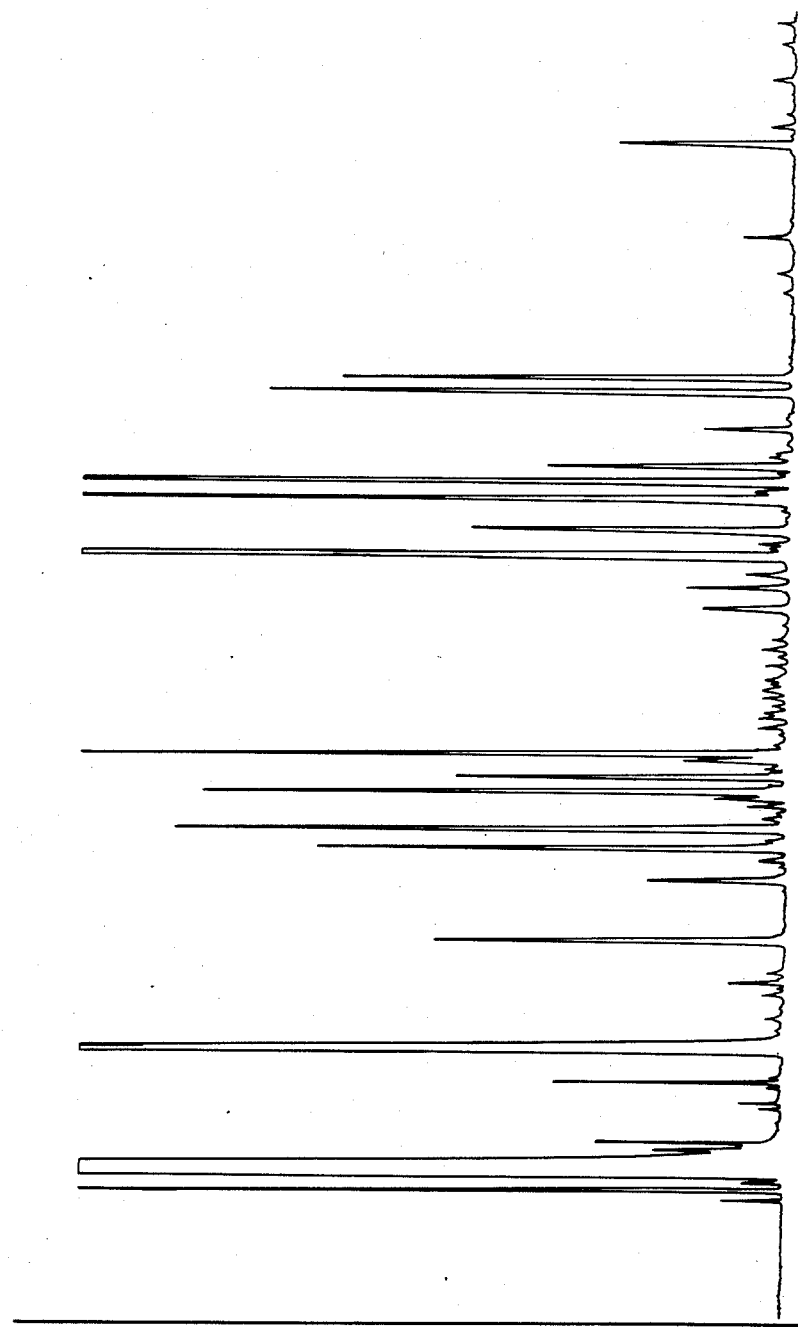
FIG. 35 is the GLC profile for perfume composition "278 m" employed in Example VI at t=3 weeks.
Figure 36:
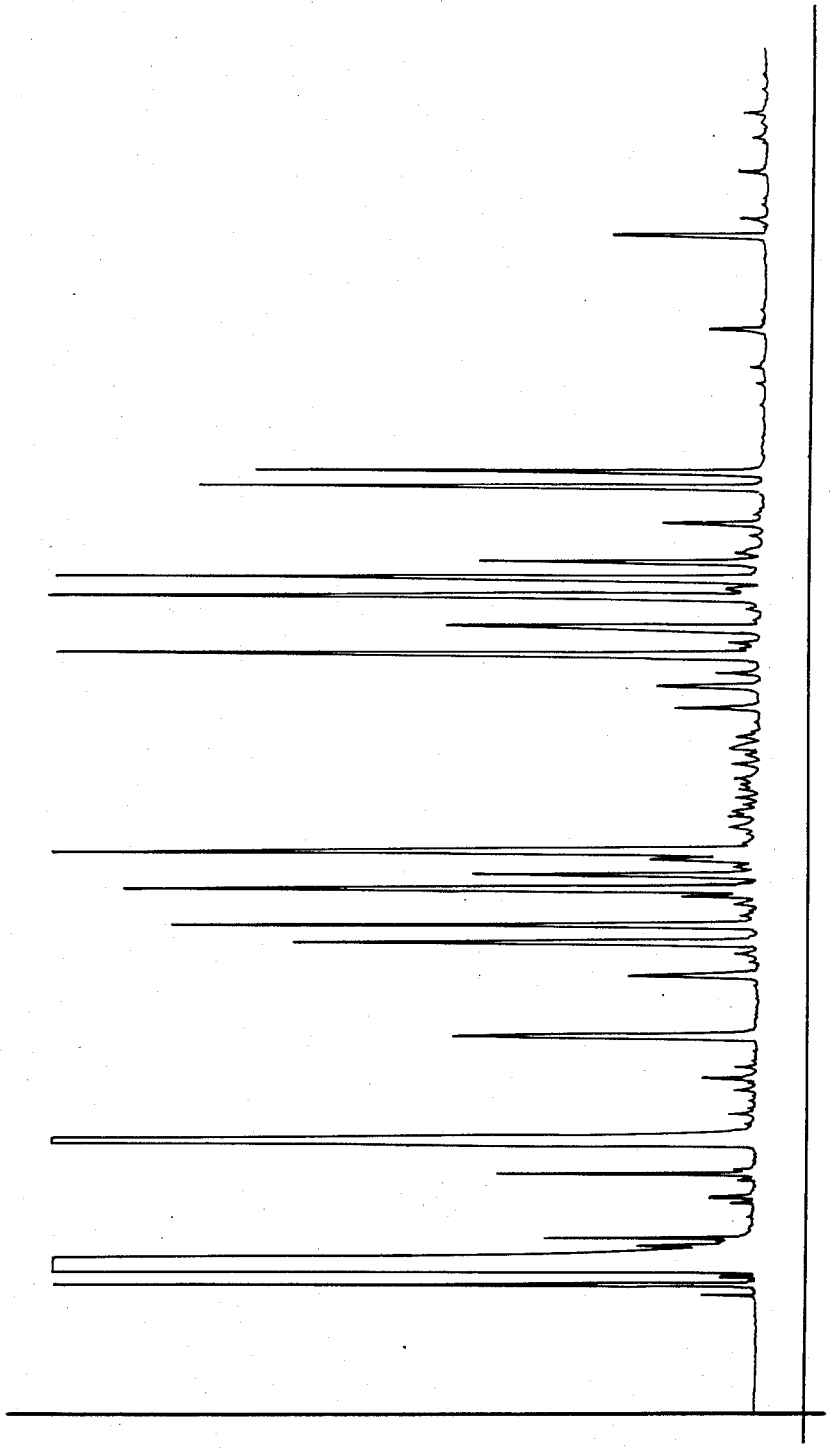
FIG. 36 is the GLC profile for perfume composition "278 m" employed in Example VI at t=4 weeks.

FIG. 29 is a perspective view of the diffusion cell which was used in order to obtain the data set forth in Examples III, IV, V and VI, infra. FIG. 31 is an exploded view of the cell of FIG. 29. Membrane 290 is placed on gland 291 and gland 291 is placed into sealed cap 293 causing the membrane 290 and the gland 291 to be firmly in place and threaded into the sealed cap 293 using lock nut 292. The sealed cap 293 previously has the liquid or gel substance the properties of which are being measured, located within it for the purpose of testing the porosity of membrane 290.

Figure 30:
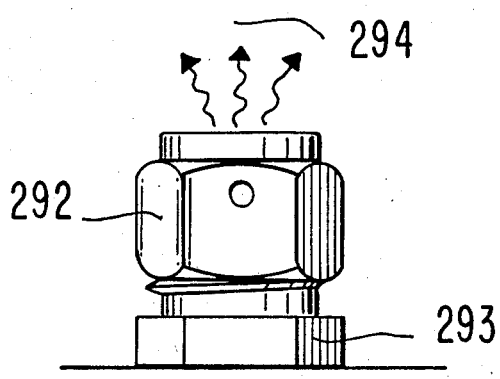
FIG. 30 is a side elevation view of the cell of FIG. 29.
Figure 32:
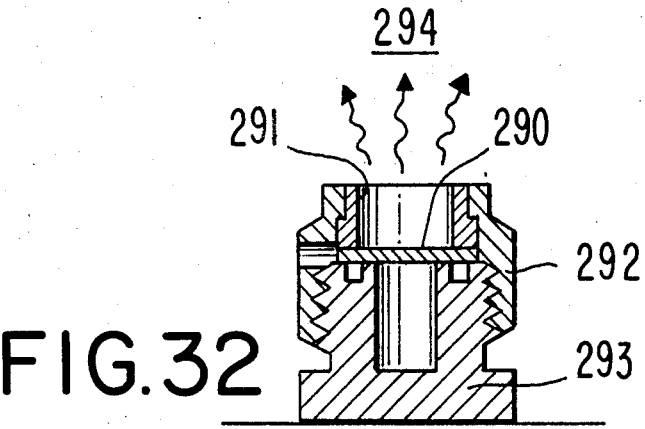
FIG. 32 is a cut-away side elevation view of the cell of FIG. 29 looking in the direction of the arrows.

During the testing, volatile substance passes through membrane 290 into the surrounding atmosphere at 294 as shown in FIGS. 30 and 32. Sealed cap 293 is shown to be screwed in place using lock nut 292 holding membrane 290 on gland 291 in FIGS. 30 and 32.

The details concerning FIGS. 26A, 26B, 26C, 27A, 27B 28 and 41 are set forth in Examples V and VI, infra.

Thus, the physical rationale or "mechanism" for operation of our invention may be (i) "a steady state" adsorption/desorption mechanism or (ii) by means of capillary action; or (iii) a combination of adsorption/desorption and capillary action. The adsorption/desorption mechanism would be operable, for example, as a result of the critical surface tension of the filler phase being greater than the critical surface tension of the volatile composition existing in the liquid state in the device of our invention.

In the case of steady state adsorption/desorption of volatile substance mass transport mechanism onto and from the microporous polymer section of the shell structure of our invention, a mathematical model may be set forth as taught by Adamson "Physical Chemistry of Surfaces", Second Edition, or Rangarajan, et al, cited supra.

Another embodiment which is preferred for the practice of our invention involves the use of a rigid rather than flexible polymer in forming rigid cylindrical containers useful for the process of our invention as illustrated in FIGS. 5, 7, 8, 9 and 10.

The process of our invention for dispensing at a controllable and visibly detectable rate, continuously or discontinuously, for discrete periods of time a volatile composition of matter from a cylindrical container 501 into the atmosphere surrounding the container in this particular embodiment comprises the steps of:

A. Entrapping the volatile composition of matter, e.g., perfume, in an entrapment agent (the entrapped material being indicated by reference numeral 11)

whereby a temporarily entrapped volatile composition is formed;

B. Placing the entrapped volatile composition 11 within cylinder 501 (that is, a first thin shell section thereto). The top of the cylinder 101 and the bottom of the cylinder 102 may be fabricated from a transparent or translucent non-porous polymer (that is, a polymer which is not porous to the volatilizable substance) whereby the presence of the volatile substance (if accompanied a color) in the inner void of the cylinder can be detected from the outside of the container so that one can easily ascertain when the entrapped volatile substance 11 is depleted (as shown by reference numeral "16" in FIG. 8). The side wall of the cylinder 12 may be fabricated from a microporous membrane as manufactured by Koninklijke Embalage Industrie Van Leer B.V. and exemplified, supra.

When not in use, the cylinder 501 containing entrapped volatile substance 11 is preferably placed in an outer cylindrical container 502 as shown in FIG. 7. The outer cylindrical container is referred to by reference numeral 502 in FIG. 7. The outer cylindrical container has a removable cap 14 which may be screwed at 103 into the lower portion 13 of said outer container 502. When the cylinder 15 is in use, the screw top 14 is removed and the inner container 15 containing the entrapped volatile composition 11 may remain in place within the outer container 502 or may be removed to a more convenient location for use. Not all of the side wall 12 need be fabricated of microporous polymer. Indeed, merely the upper third or the upper quarter or the lower quarter of the side wall or even the top or the bottom of the cylindrical container may be fabricated from microporous polymer, the remainder of the container 15 shell being fabricated using a transparent substance which is rigid or flexible or using a silicate or quartz glass.

Another embodiment of the cylindrical hollow structure which is illustrative of our invention is set forth in FIGS. 9 and 10 wherein the upper portion of the cylindrical structure 17 may be screwed into the lower portion of the structure 18 at screw threads 20. Thus, structure 503 containing volatile substance 19 may be manufactured in a form which is reusable when the volatile substance 19 is depleted down to the remaining depleted gel (or other entrapment substance) 21 as indicated in FIG. 10. Conveniently, lower portion 18 may be fabricated from a transparent substance such as transparent rigid polypropylene or glass and upper portion 17 may be fabricated from a microporous polymer, e.g., microporous polyurethane or polypropylene containing a filler, e.g., talc or $CaCO_3$ and may be perpetually opaque or opaque only when cylinder 503 is not in use. Thus, when volatile substance 19 is depleted down to depleted substance 21 the upper portion 17 of cylinder 503 in FIGS. 9 and 10 may be temporarily removed and additional substance 19 may be added to the lower portion 18. Structure 503 in FIGS. 9 and 10 may then be replaced into a larger cylinder to form a structure such as that illustrated in FIG. 7, the purpose of which is for storage; until it is decided to reuse the structure 503.

Figure 5:
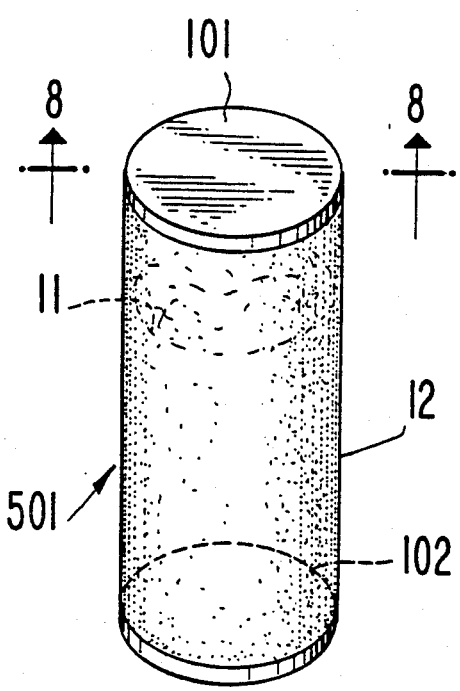
FIG. 5 is a perspective view of a second preferred embodiment of the structure in accordance with our invention with a hollow cylinder fully loaded immediately prior to functional use thereof.

The following examples serve to illustrate embodiments of our invention as it is now preferred to practice it with reference to using volatile materials, e.g., air freshener/perfume compositions in conjunction with the hollow totally enclosed structures of our invention as illustrated in FIGS. 1, 5 and 9. It will be understood that these examples are illustrative and that the invention is to be restricted thereto only as defined in the appended claims.

EXAMPLE I

Into compartment 6, onto surface 4 of the structure 500 illustrated in FIGS. 1, 2 and 3 is placed a composition prepared as follows: 3.0 parts by weight of Carbopol® 940 (manufactured by the B. F. Goodrich Company) (see Note 1) is sifted into the vortex of rapidly stirring water (88.8 parts by weight) containing 0.2 parts by weight of methyl paraben at a temperature of 22° C. The mixing is continued until a smooth cloudy dispersion is formed. 2.0 Parts by weight of a perfume composition (see Note 2) is added to the prepared slurry and the slurry is continued to be mixed until the perfume composition is dispersed. The slurry is then neutralized with 6.0 parts by weight of diisopropanolamine (50% solution in water) using slow mixing to avoid the inclusion of air. The structure 500 is then sealed along the circumferential edges at location 1 as shown in FIGS. 1, 2 and 3 and use of the structure resulting therefrom is shown in accordance with the graph referenced by reference numeral "202" in FIG. 18. When instead of the perfume (Note 2), only ethyl alcohol is used as the volatilizable material, the operation of structure 500 is in accordance with the graph indicated by reference numeral "201" in FIG. 18. It will be noted that for periods of use, structure 500 operates at steady state very soon after (5 minutes) use is commenced.

Note 1: Carbopol® 940 is produced by the B. F. Goodrich Chemical Company of 3135 Euclid Avenue, Cleveland, Ohio. It is identified as a carboxyvinyl polymer of high molecular weight.

Note 2: The formulation of the fragrance is as follows:

| Ingredients | Parts by Weight |
| --- | --- |
| Para cresol | 1 |
| Methyl jasmonate | 100 |
| Acetyl methyl anthranilate | 20 |
| Farnesol | 4 |
| Cis-3-hexenyl benzoate | 30 |
| Nerolidol | 30 |
| Indol | 15 |
| Eugenol | 20 |
| Benzyl alcohol | 40 |
| Methyl linoleate | 40 |
| Jasmin lactone | 20 |
| Dihydromethyl jasmonate | 10 |
| Linalool | 150 |
| Benzyl acetate | 400 |
| Abietyl alcohol | 150 |
| Cis jasmone | 150 |

The evaporating surface in hollow structure 500 is 8 square inches; and the weight of entrapped volatile substance 3 is 30 grams.

EXAMPLE II(A)

3.0 Parts by weight of Carbopol® 940 (manufactured by the B. F. Goodrich Company) is sifted into the vortex of 44.4 parts rapidly stirring ethyl alcohol and 44.4 parts of distilled water. Mixing is continued until a smooth, cloudy dispersion is formed. 2.0 Parts by weight of the perfume of Example I is then added to the prepared slurry and mixing is continued until the perfume is dispersed. The slurry is then neutralized with 6.0 parts by weight of diisopropanolamine (50% solution in water) using slow mixing to avoid inclusion of air at a temperature of 22° C. The resulting gel is then placed into cylinder 501 of FIG. 5. The use of this air freshener cylinder is in accordance with the graph indicated by reference numeral "204" in FIG. 18. Without the use of the perfume composition of Example I, the cylindrical shell of FIG. 5 operates in accordance with the graph indicated by reference numeral "203" in FIG. 18. In both cases, the percent volatiles lost during Example I (but using ethanol, instead), the cylindrical shell of FIG. 5 operates in accordance with the graph indicated by reference numeral "203" in FIG. 18. In both cases, the percent volatiles lost during operation of the cylinder 502 is in accordance with a steady mass transport mechanism can be observed from the graphs 201, 202, 203 and 204 of FIG. 18.

When the gel of this example is simply used in a commercial air freshener (in the air freshener of U.S. Pat. No. 4,014,501), the mass transport mechanism is "unsteady state" in accordance with the graph indicated by reference numeral 205 in FIG. 18.

EXAMPLE II(B)

83.45 grams of distilled water is heated to 85° C. With rapid agitation on a propeller type mixer, Gelcarin ® AFG-15 (carageenan prepared by the Marine Colloids Corporation) is dispersed in the water. 3.50 grams of glycerine is slowly added to the carageenan dispersion. The mixture of glycerine and carageenan is then reheated and combined with 2.0 parts by weight of the perfume composition of Example I and 8.00 parts by weight of Tween ® 80 (a trademark of I.C.I. America) (see Note 3). 0.05 parts by weight of formaldehyde is then added to the resulting mixture slowly and the resulting material is then poured into the cylinder of FIG. 9. It is material is then poured into lower portion 18 of cylinder 503 of FIG. 9. The lower portion 18 of cylinder 503 is then sealed at 20 with upper portion 17 and placed in use.

The graph indicated by reference numeral 301 indicates the length of time of usefulness of the resulting cylinder; a "steady state" mass transport mechanism for the use of cylinder 503 as an air freshening apparatus.

When the composition prepared above is used in accordance with a standard air freshener package (per U.S. Pat. No. 4,014,501), the rate of fragrance loss is shown in accordance with the graph indicated using reference numeral 302 in FIG. 19 (an unsteady state mass transport mechanism rather than the steady state mass transport mechanism of graph 301 in FIG. 19).

Note 3: Tween ® 80 is a mixture of oleate esters of sorbitol and sorbitol anhydrides consisting predominantly of the monoester condensed with approximately 20 moles of ethylene oxide in accordance with the formula:

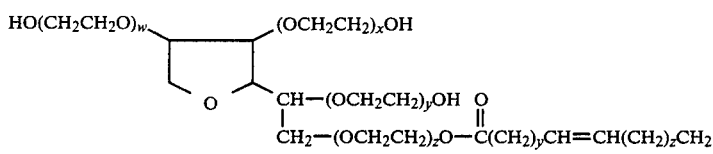

wherein $w+x+y+z$ has an average value of 20.

EXAMPLE III(A)

Into a group of three jars indicated as (i), (ii) and (iii) each having an opening having an area of of 15.48 cm², a height of 4.2 cm, an opening diameter of 4.4 cm and an internal diameter of 4.8 cm (total volume: 72.5 cc) is placed 5000 mg (5 grams) of the following perfume composition:

| Ingredients | Parts by Weight |
|---|---|
| Citrus oil distilled | 275 |
| Dipentene | 150 |
| The mixture of compounds having the structures: | 130 |

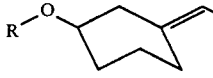

and

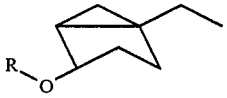

prepared according to U.S. Letters Pat. No. 4,330,416 issued on May 18, 1982 (the specification for which is incorporated by reference herein)

| | |
|---|---|
| Geraniol | 50 |
| Tetrahydro Muguol | 50 |
| Lemon oil | 50 |
| Grapefruit oil | 50 |
| Geranonitrile | 25 |
| n-Octanal | 20 |
| n-Nonanal | 20 |
| n-Decanal | 10 |
| Citronellol | 10 |
| 1-(4-Pentenoyl)-3,3-dimethyl cyclohexane | 25 |
| Beta pinene | 5 |
| n-Nonanol | 20 |
| Cis-3-hexenyl formate | 5 |
| Cis-3-hexenol | 10 |
| Methyl jasmonate | 25 |
| Dihydro methyl jasmonate | 20 |

Jar (i) is left open and the evaporation of the above fragrance formulation is measured on a daily basis.

Jar (ii) is covered in a tight fitting manner with a membrane having the following specifications:

| | |
|---|---|
| Composition | Polypropylene + CaCO₃ filler |
| Thickness | 100 micrometers |
| Weight | 90 g/m² |
| Ultimate tensile strength | 30 MN/m² (machine direction) |
| | 11 MN/m² (transverse direction) |
| Elongation at break | 180% (machine direction) |
| | 350% (transverse direction) |
| Pore size | 0.2 micrometers (max) |
| Void volume | 0.34 cm³/g (30%) |
| Density | 900 kg/m³ |
| Air flow | 3 cm³/cm²/min at 1 kg/cm² |

| | -continued |
|---|---|
| Water flow | 0.001 cm³/cm²/min at 1 kg/cm² |
| Air resistance (Gurley) | 8,000 seconds |
| Water vapor transmission | 150 g/m²/24 hrs at 23° C. at 50% relative humidity |
| Thermal stability | 10 hrs at 130° C. |

Jar (iii) is covered in a tight fitting manner with a polypropylene film of 1 mil thickness. In each of the jars the rate of evaporation of the fragrance is measured on a daily basis. The weight loss occurs at constant temperature, 22° C. and constant relative humidity, 50% relative humidity.

Table I set forth below shows weight loss as a function of time and weight loss per square centimeter as a function of time for each of jars (i), (ii) and (iii).

TABLE I

| | JAR (i) | | JAR (ii) | | JAR (iii) | |
|---|---|---|---|---|---|---|
| Days | mg of perfume composition lost | mg/cm² of perfume compositon lost | mg of perfume composition lost | mg/cm² of perfume composition lost | mg of perfume composition lost | mg/cm² of perfume composition lost |
| 1 | 130 | 12.3 | 80 | 5 | 20 | 1.3 |
| 2 | 470 | — | 150 | — | 50 | — |
| 3 | 630 | 45.0 | 230 | 15 | 80 | 5.0 |
| 6 | 1070 | 69.0 | 370 | 24 | 120 | 8.0 |
| 7 | 1330 | — | 430 | — | 140 | — |
| 9 | 1850 | 119.0 | 560 | 36 | 200 | 13.0 |
| 15 | 2310 | 149.0 | 880 | 57 | 310 | 20.0 |
| 31 | 2660 | 172.0 | 1450 | 94 | 600 | 39.0 |
| 36 | 2740 | 177.0 | 1560 | 100 | 680 | 44.0 |

EXAMPLE III(B)

Three jars are provided, Jar (iv), Jar (v) and Jar (vi) having dimensions identical to those of Example III(A). To each of the jars, 20 grams of a perfumed gel is added which is prepared as follows:

"3.0 Parts by weight of Carbopol ® 940 (manufactured by the B. F. Goodrich Company) (see Note 1 of Example I) is sifted into the vortex of rapidly stirring water (88.8 parts by weight) containing 0.2 parts by weight of methyl paraben at a temperature of 220° C. The mixing is continued until a smooth cloudy dispersion is formed. 2.0 Parts by weight of the perfume composition of Example III(A) is added to the prepared slurry and the slurry is continued to be mixed until the perfume composition is dispersed. The slurry is neutralized with 6.0 parts of weight of diethylpropenol-amine (50% solution in water) using slow mixing to avoid the inclusion of air."

Jar (iv) is permitted to remain open while measurements for weight loss of gel are made on a daily basis.

Jar (v) is tightly covered with a membrane having the same specifications as the membrane used to cover Jar (ii) in Example III(A) and the weight loss is measured on a daily basis.

Jar (vi) is covered with a polypropylene film having a thickness of 1 mil and the weight loss of the gel is measured on a daily basis.

Table II, below sets forth weight loss as measured in mg/cm² for each of Jars (iv), (v) and (vi):

TABLE II

| Days | JAR (iv) (mg/cm²) | JAR (v) (mg/cm²) | JAR (vi) (mg/cm²) |
|---|---|---|---|
| 1 | 134 | 28 | 0.7 |
| 3 | 555 | 113 | 2.0 |
| 6 | 1007 | 219 | 2.0 |
| 9 | 1201 | 349 | 3.9 |
| 15 | 1207 | 570 | 4.5 |
| 31 | 1210 | 1083 | 9.0 |
| 36 | 1209 | 1154 | 9.7 |

FIG. 43 is a graphical representation of the results set forth in Table II, supra. The graph indicated by reference numeral "420" is the graph for the open jar, Jar (iv) (mg/cm² vs. time). The graph indicated by reference numeral "421" is the graph for the weight loss of gel from Jar (v). The graph indicated by reference numeral "422" is the graph for the weight loss of gel from Jar (vi) as a function of time.

EXAMPLE IV(A)

The following experimental design was established through an evolutionary process in order to determine the permeability of water vapor through filled polypropylene film as exemplified hereinbefore.

I. Cell Design

Stainless steel 316 diffusion cells as illustrated in FIGS. 28-31, inclusive the details for which are set forth, supra, were specially designed to measure the transport of small amount of water vapor through a film sample under controlled experimental conditions. Commercially available fittings (nut, plug and glands) were modified to accommodate water or a volatile substance in one side of the gland and a film specimen between the two glands.

II. Materials

A. Films: A film designated as having a nominal air transport rate of 12,000 Gurley seconds (Gs) was employed. Six samples, each measuring 6"×6", were cut from the center of a 10" wide stock sample. From each of these test samples, a sample approximately 2.0 cm in diameter was used for the permeation experiments and a sample of approximately 5" diameter was used for air permeation measurements. Approximately 0.5 g of water were used in each of the test cells.

B. Silylation procedure: Trimethylsilyl chloride (20 gms) was placed in a 200 ml beaker and placed in a glass desicator. Three of the 6"×6" test samples were suspended inside of the desicator and the desicator was closed tightly and placed in a 45° C. oven overnight. The beaker was then removed from the desicator after it returned to ambient temperature. The desicator was then evacuated at approximately 20 mm/Hg for a period of 4–5 hours to remove residual volatiles. The films were then used for the experimental procedure.

C. Water: Approximately 0.5 g of water were used in each of the test cells.

III. Environmental Conditions

A. Oven: A Blue "M" controlled temperature and humidity oven was used for all experimental conditions. The temperature and humidity conditions were controlled by the dry and wet bulb thermometers located inside of the test chamber.

B. Conditions: The following conditions were used in the experiments:

| Temperature (°C.) | 25 | 30 | 35 | 40 | 45 | 50 | 55 |
|---|---|---|---|---|---|---|---|
| Relative Humidity (%) | 50 | 63 | 72 | 78.5 | 83.5 | 89 | 90 |

These conditions established a relative water vapor pressure difference of 15.85 mb between the inside and outside of the cell.

C. Temperature conditions: The following sequences of temperatures (°C.) were employed to randomize the sample treatments and reduce possible systematic error:

(A) 25–45–30–40–55–35–25–35° C.
(B) 35–50–30–45–25–35–40–25–30° C.

IV. Sample Weighing

The cells were placed in the oven at the selected temperature condition so that the film was in the "up" position as indicated in FIGS. 30 and 31. After the samples were equilibrated for at least 10–12 hours, the samples were weighed using a Mettler AE-163 electronic balance interfaced to the Digital Equipment Corporation (Maynard, Mass.) VAX®11/780 computer. The samples were then replaced in the oven and were reweighed after approximately 12 hours to give the transport rate for each condition. Five replicates were run and samples were re-tested at 25°, 30° and 35° C. to monitor reproducibility.

V. Data Handling

All data were entered directly into the Vax 11/780 computer using specified software in order to facilitate the calculation of weight-loss, the plotting of graphs, and the manipulation for computational purposes.

VI. Experimental Details

Experiment using 8,000 Gs and 12,000 Gs films, regular and silylated, at 25° C. (50% R.H.), 35° C. (71% R.H.) and 45° C. (83% R.H.).

In FIG. 25 (which is a plot of transport rate of water vapor versus temperature and degrees centigrade) the graph indicated by reference numeral "250" is a graph of transport rate versus temperature for 8,000 Gurley second film which is not treated (silylated).

The graph indicated by reference numeral "251" is a graph of transport rate versus temperature for water loss from a silanized 8,000 Gurley second film for the three temperatures, 25° C., 35° C. and 45° C.

The graph indicated by reference numeral "253" in FIG. 25 is a graph of transport rate versus temperature in degrees centigrade for rate of water loss from a nominally 12,000 Gurley second filled polypropylene film at temperatures of 25° C., 35° C. and 45° C.

The graph indicated by reference numeral "252" in FIG. 25 shows transport rate versus temperature in degrees centigrade for rate of water loss from a silanized nominally 12,000 Gurley second film at 25° C., 35° C. and 45° C.

The results of this study are:

(i) Diffusion of water through a filled polypropylene matrix (membrane defined according to the properties set forth hereinbefore) does not contribute significantly to the mechanism of the total transport through said film;

(ii) A "high" activation energy process (such as viscous capillary flow) appears to contribute significantly to the transport of water through the filled polypropylene films especially above 40° C.; and (iii) A "low" activation energy process (such as sorption-driven surface flow) appears to contribute significantly to the transport of water through the filled polypropylene films especially below 40° C.

EXAMPLE IV(B)

The following Table III shows the air resistance rating of 15 films measured in Gurley seconds and the minimum and maximum water transport rates that were observed at 25° C. and at 50% relative humidity. The measurements were carried out using cells and procedures substantially as described in Example IV(A), supra.

TABLE III

| | WATER TRANSPORT AT 25° C. | | |
|---|---|---|---|
| Film No. | Air Resistance (Gurley seconds) | Minumum Water Transport Rate (g/m²/day) | Maximum Water Transport Rate (g/m²/day) |
| 1 | 1600 | 370 | 683 |
| 2 | 2100 | 508 | 667 |
| 3 | 3100 | 434 | 603 |
| 4 | 3200 | 249 | 593 |
| 5 | 3300 | 439 | 651 |
| 6 | 4000 | 376 | 481 |
| 7 | 4300 | 339 | 751 |
| 8 | 4300 | 413 | 677 |
| 9 | 5400 | 143 | 481 |
| 10 | 6000 | 140 | 344 |
| 11 | 6700 | 243 | 333 |
| 12 | 7000 | 249 | 608 |
| 13 | 7100 | 222 | 280 |
| 14 | 10200 | 222 | 317 |
| 15 | 10800 | 169 | 193 |

EXAMPLE V

Materials

A. TEST PRODUCTS: Eight samples of the articles as illustrated in FIG. 5.

B. TEST CHAMBERS: The test chambers were constructed from white polypropylene canisters of 5 gallon liquid volume which has been fitted with an air-tight lid. The lid had a 2 inch evaluation hole cut in the middle which was fitted with a cork stopper. Individual samples were placed in the chambers approximately 1 hour prior to evaluation to permit equilibration.

C. JUDGES: A panel of 23 individuals trained and skilled in the practice of magnitude estimation were employed as odor intensity judges. The judges provided ratio-scaled assessments of the perceived odor intensity.

D. CONTROL SAMPLES: The following control samples were incorporated into the experimental design:
1. 100 g Unfragranced Gel, fully exposed from a petri plate, the gel being prepared in accordance with the process of Example III(B).
2. 100 g Fragranced gel ("894 m"), fully exposed from a petri plate (prepared according to the procedure of Example III(B).

E. SAMPLE EXPOSURE: Duplicate samples were scheduled for ambient room exposure based upon a converging depletion design so that samples representing 0, 2, 3, and 4 weeks of exposure were available at the date of the sensory test.

Methods

All exposed samples were submitted in the blind to the panel of judges after 1 hour in the test chambers. A total of 22 samples were evaluated in the test. All test samples were randomized upon submission to the judges and re-randomized periodically throughout the evaluation period.

The magnitude estimation sensory data (reference: Warren, C. B., Paper No. 3 "Development Of Fragrances With Functional Properties By Quantitative Measurement Of Sensory And Physical Parameters"; Moskowitz and Warren "Odor Quality And Chemical Structure", American Chemicals Society Symposium Series 148 (American Chemical Society—Washington, D.C., 1981) was normalized by the method of "no standards". Standard errors of the measurements were calculated to determine the significance of the perceived test sample intensities.

Analytical Data

Figure 26A:
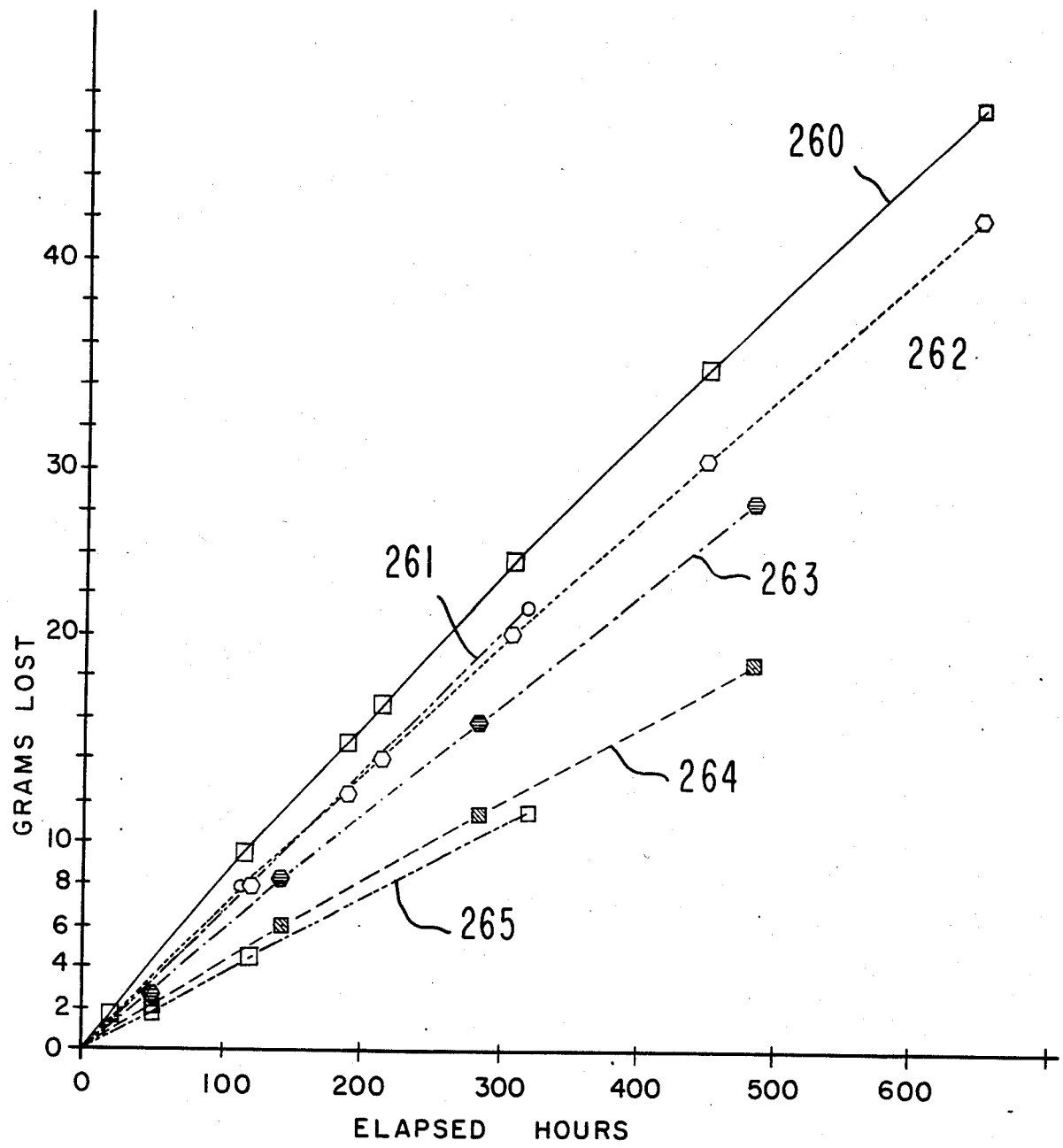
FIG. 26A is a series of graphs of time (elapsed hours) vs. grams water and fragrance lost from the article illustrated in FIG. 5 using various temperatures of operation. The data points are set forth in Example V, infra.
Figure 26B:
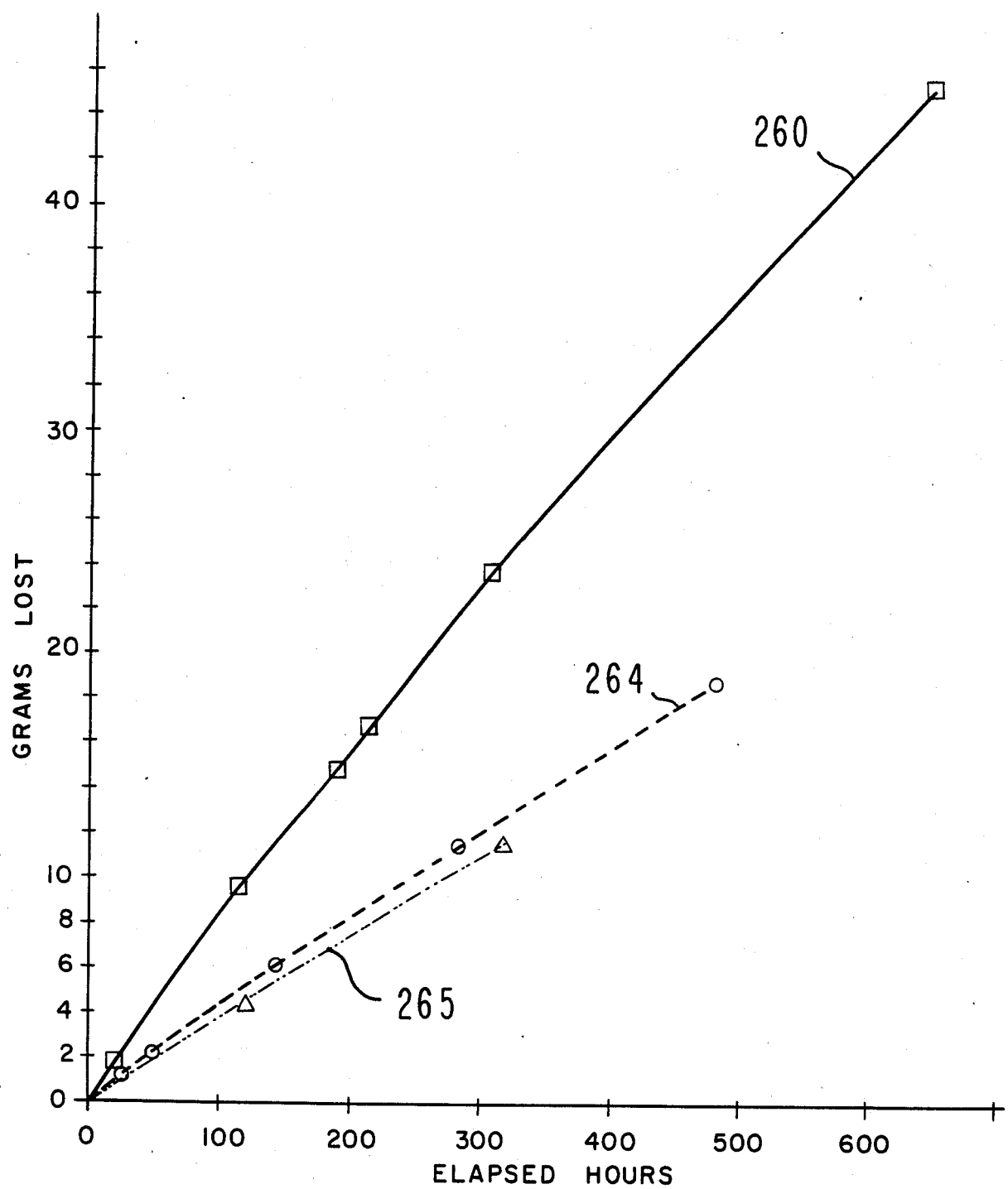
FIG. 26B is also a series of graphs of time (elapsed hours) vs. grams water and fragrance lost from the article illustrated in FIG. 5 using various temperatures of operation and working specifically with a fragrance identified as "278m". The method of obtaining such data is further specified in Example V, infra.
Figure 26C:
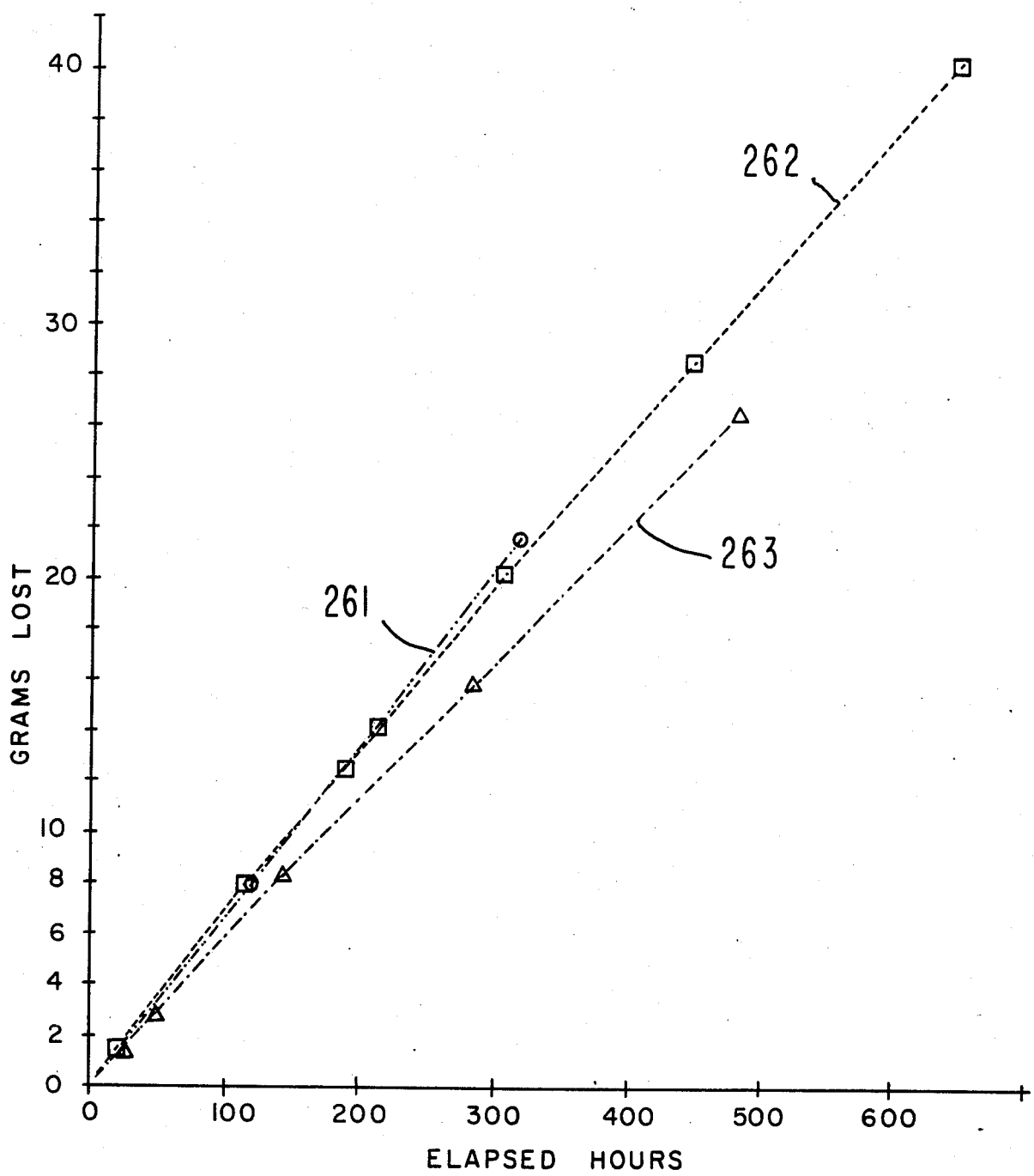
FIG. 26C is a series of graphs of time (elapsed hours) vs. grams water and fragrance lost from the article illustrated in FIG. 5 using various temperatures of operation and particularly working with the fragrance indicated at 37894m" in Example V, infra.
Figure 27:
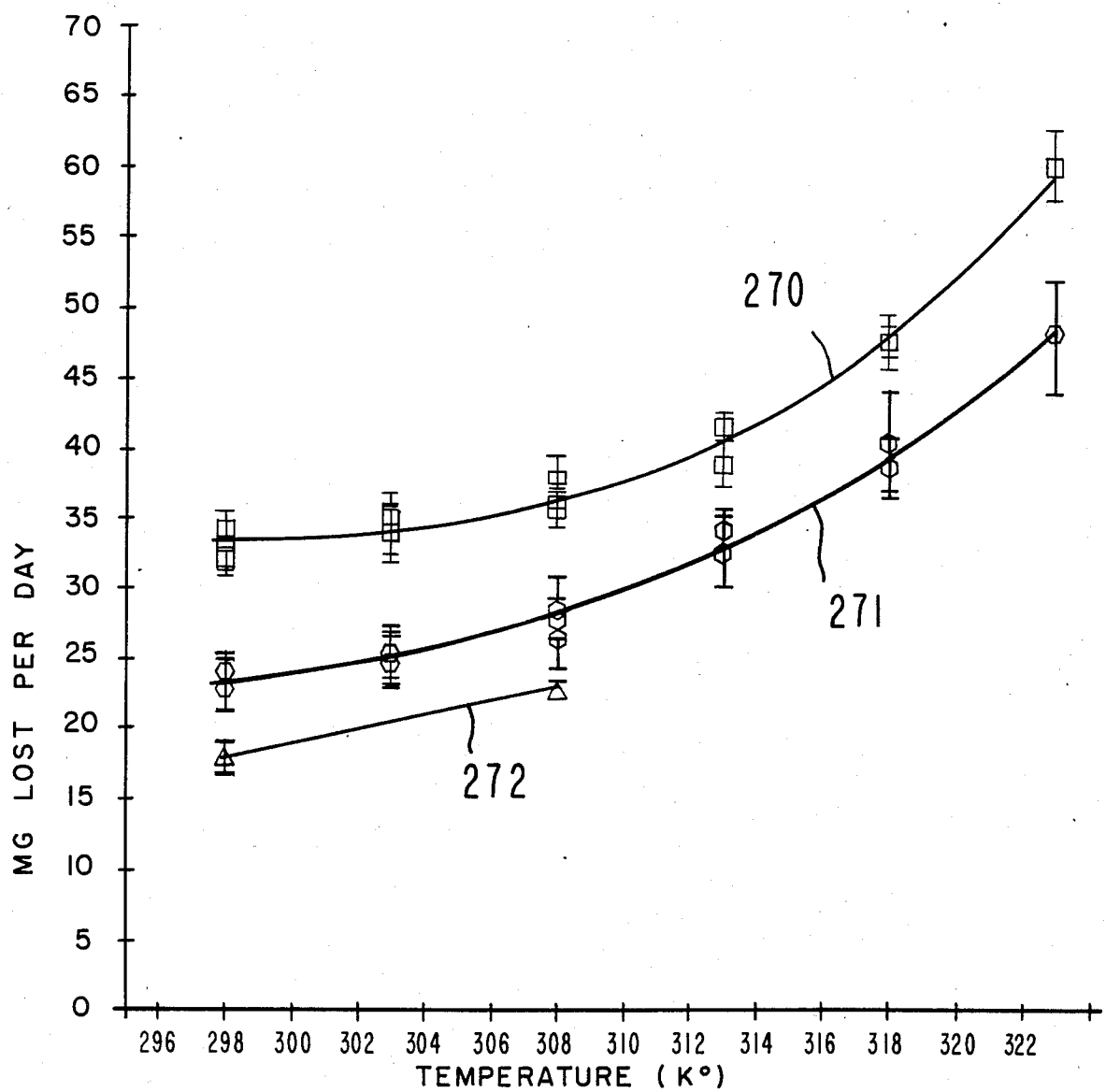
FIG. 27A sets forth graphs showing water transport through filled microporous polymeric membranes useful in the practice of our invention; and these graphs set forth mg. water lost per day vs. temperature in degrees Kelvin.
FIG. 27B sets forth a graph showing water transport through filled microporous polymeric membranes useful in the practice of our invention; and this graph sets forth grams water lost per day per square meter vs. temperature in degrees Kelvin.
Figure 27B:
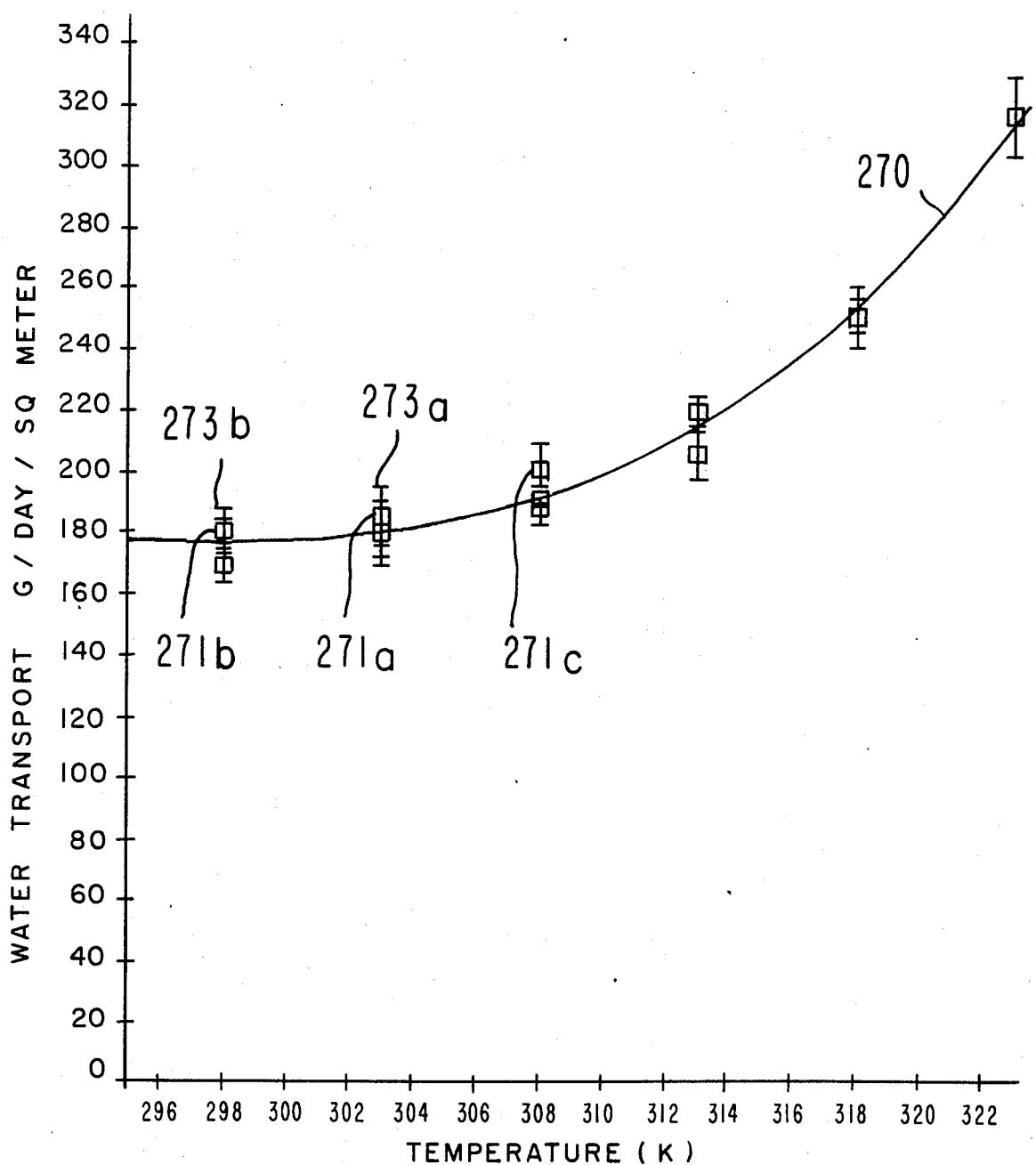
Figure 28:
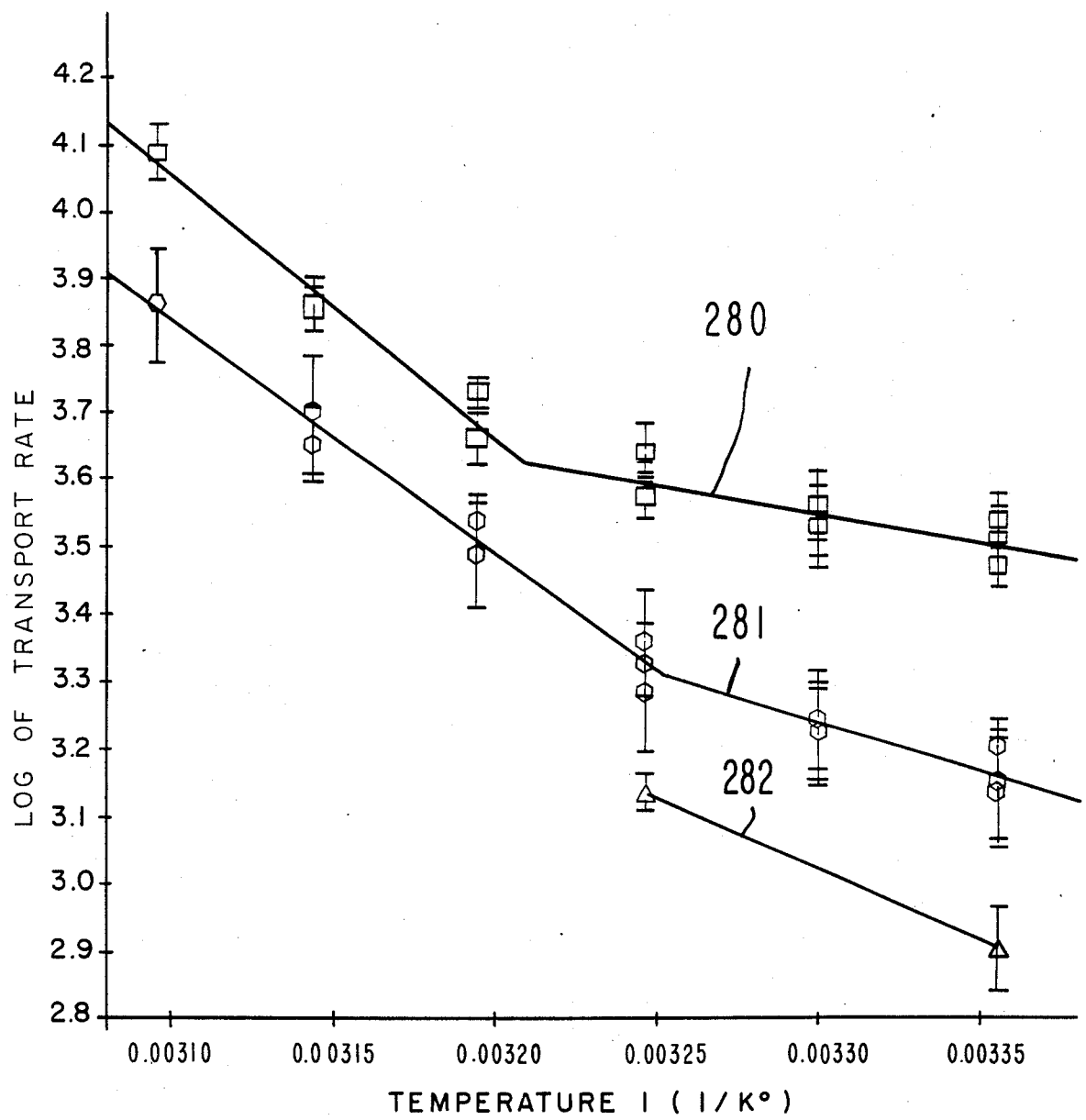
FIG. 28 is an Arrhenius Plot of the data set forth in FIG. 27A and sets forth the log (natural base) of transport rate vs. reciprocal temperature (degrees Kelvin$^{-1}$).

The cumulative weight-loss was obtained during the exposure period for each of the test samples (excluding the controls and the zero-time samples). The periodic weighings were compiled and reported as Cumulative Weight-loss vs. time and this is shown in FIGS. 26A, 26B and 26C.

Results

The summarized sensory testing results are presented for fragrance "894 m" in Table IV, infra. The normalized product weight-loss data for "894 m" are incorporated into the last two columns of this Table (IV) and reported graphically in FIGS. 26A, 26B and 26C.

The graph indicated by reference numeral "260" is the graph showing grams loss of gel vs. time for four weeks of exposure gel containing fragrance "278 m".

The graph indicated by reference numeral "262" is the graph showing the mean weight loss after 4 weeks of exposure for the gel containing fragrance "894 m".

The graph indicated by reference numeral "264" is the graph showing the mean weight loss rate for gel containing fragrance "278 m" after 3 weeks.

The graph indicated by reference numeral "263" is the graph showing the mean weight loss of a gel containing fragrance "894 m" after 3 weeks.

The graph indicated by reference numeral "265" is the graph showing the mean weight loss of a fragranced gel containing fragrance "278 m" after 2 weeks exposure.

The graph indicated by reference numeral "261" is the graph of the mean weight loss of a gel containing fragrance "894 m" after 2 weeks exposure.

Graphs 260, 264 and 265 are shown separately on FIG. 26B.

Graphs 261, 262 and 263 of FIG. 26A are shown separately in FIG. 26C.

Discussion

The results of the sensory experiments suggest that there is a critical equilibration point sometime between "zero" and 2 weeks. This is reflected in the intensity decay between these two evaluation points in this experiment.

The product containing fragrance "894 m" did not show any significant perceived odor intensity decay over the period of 2 thru 4 weeks of exposure.

Summary

The results of this study indicate that the product fragranced with "894 m" quickly equilibrates to what is perceived as a "steady-state" fragrance delivery rate over a 4 week period.

TABLE IV

QUANTITATIVE OF ODOR "EVALUATION OF FRAGRANCE" "894 m" BY MAGNITUDE ESTIMATION

Fragrance: "894 m"
No. of Panelists: 23

| Sample Indent. | Exposure Time | Mean Intensity[b] | Std. Error[a] | Average Intensity | Std. Error[a] | mg/hr. Frag. Loss Nom./Ave. | |
|---|---|---|---|---|---|---|---|
| Control | | | | | | | |
| Fragranced Gel | 0 hrs. | 80.3 | 1.05 | | | — | — |
| | | 77.5 | 1.05 | 78.89 | 1.04 | | |
| Zero Time | 16 hrs. | 53.1 | 1.13 | | | — | — |
| | | 52.6 | 1.10 | 52.87 | 1.08 | | |
| 2 Weeks | 319 | 43.0 | 1.07 | | | 66.4 | |
| | | 44.9 | 1.10 | 43.94 | 1.06 | 68.7 | 67.6 |
| 3 Weeks | 482 | 51.1 | 1.05 | | | 54.2 | |
| | | 41.1 | 1.12 | 45.83 | 1.06 | 55.8 | 55.0 |
| 4 Weeks | 646 | 36.1 | 1.09 | | | 59.5 | |
| | | 57.0 | 1.05 | 45.36 | 1.05 | 65.8 | 62.6 |

[a]Geometric means are calculated for all intensities. Standard errors should be read as 1. + % error, e.g., 1.13 = 13% relative error.
[b]A moderate odor intensity has a value of 30 on this scale.

EXAMPLE VI

Air Freshener Products

Materials

Air fresheners produced according to Example V and used in said Example V were then utilized for this example.

GLC analysis was performed on dual 50 meter fused silica capillary columns containing OV-1 or Carbowax 20M liquid phases.

Methods

Aliquots of the test samples were prepared for analysis by placing 5 grams of sample, in a shaker jar with 25 mls of food grade ethanol and shaking on a wrist-action shaker for approximately 24 hours until no additional color could be removed from the gelatinous residue. The ethanol solution was quantitatively decanted and the gelatinous residue was washed with an additional 10 ml of food grade ethanol. The extract and wash were combined, diluted volumetrically to 50 ml and filtered using a Milipore ® filter.

Results

GLC analysis of the isolates confirmed that the profile of the isolate was consistent with that of the original fragrance oil.

Figure 37:
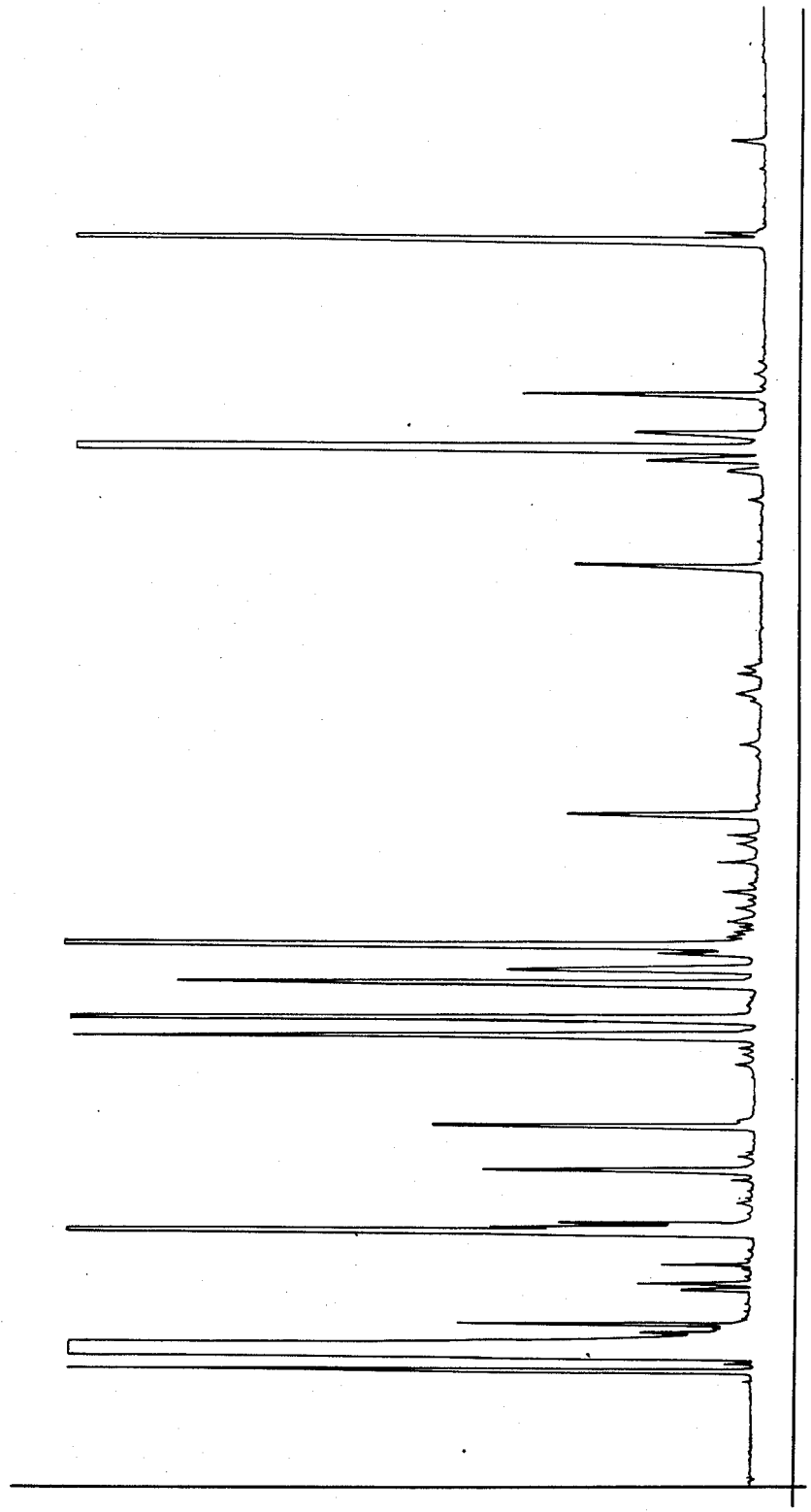
FIG. 37 is the GLC profile for perfume composition "894 m" employed in Example VI at t=0 weeks.
Figure 38:
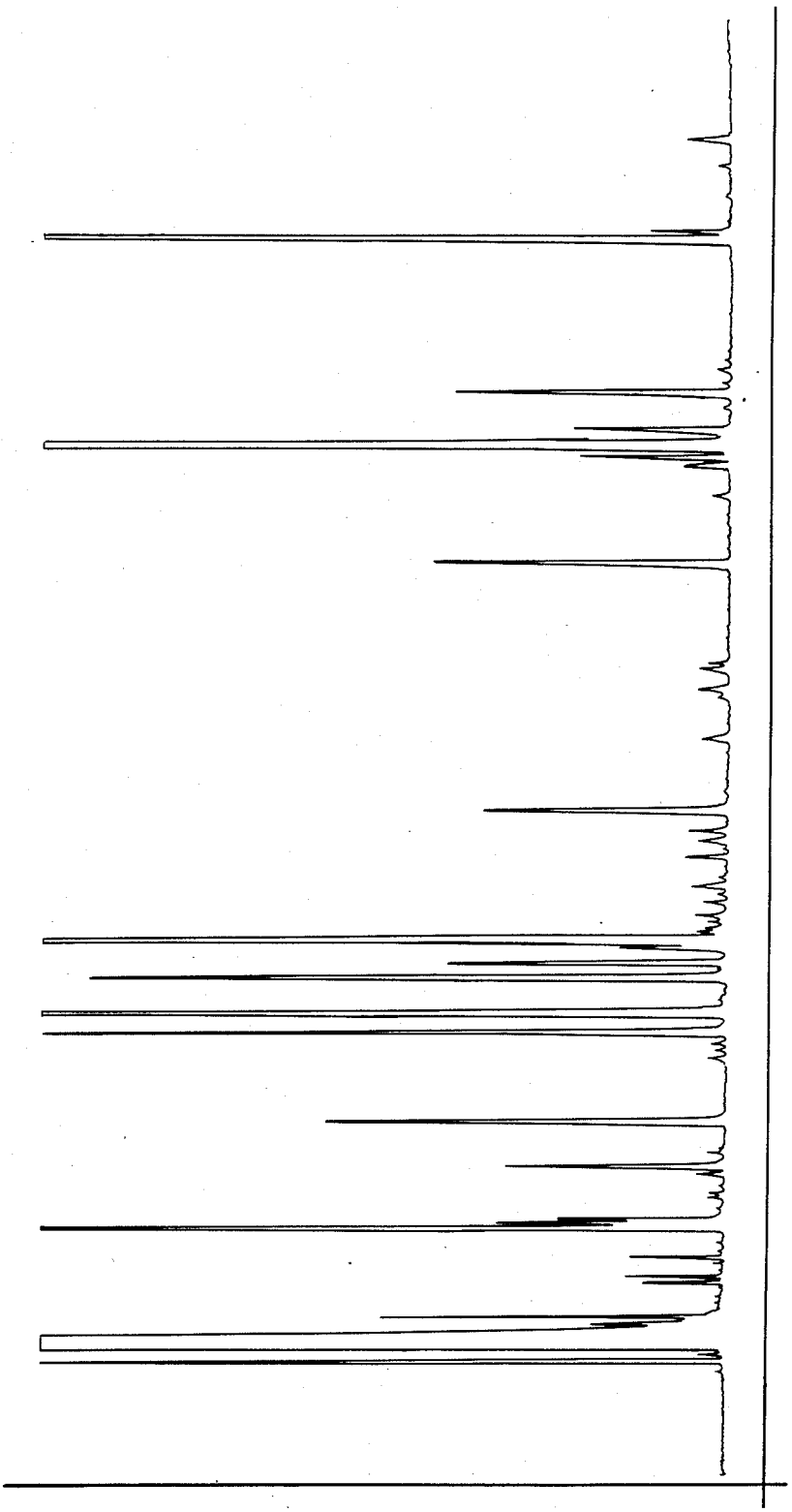
FIG. 38 is the GLC profile for perfume composition "894 m" employed in Example VI at t=2 weeks.
Figure 39:
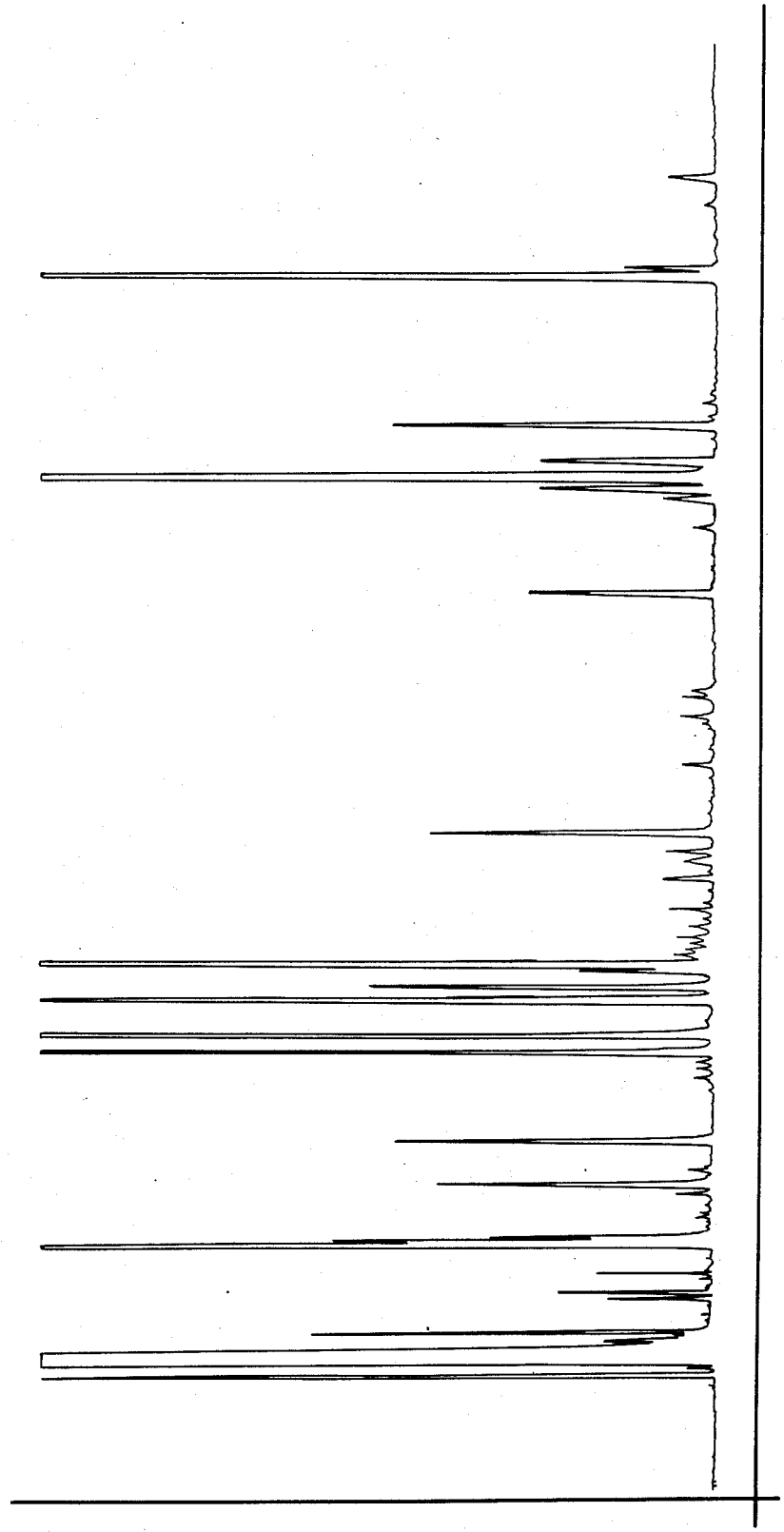
FIG. 39 is the GLC profile for perfume composition "894 m" employed in Example VI at t=3 weeks.
Figure 40:
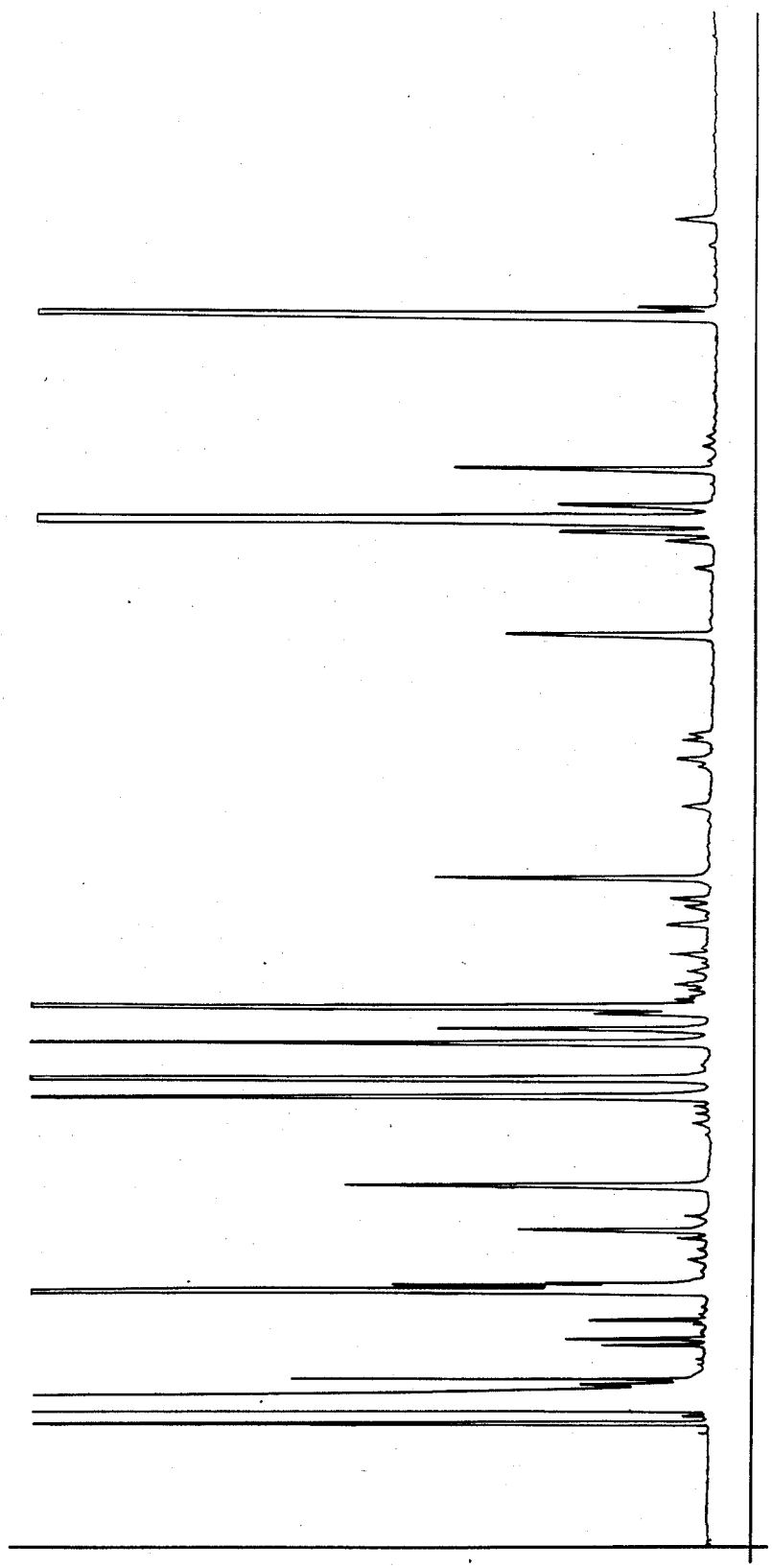
FIG. 40 is the GLC profile for perfume composition "894 m" employed in Example VI at t=4 weeks.

The results of the internal standard GLC analyses are presented (a) for fragrance 278 m on Carbowax 20M in FIGS. 33 (0 weeks), 34 (2 weeks), 35 (3 weeks) and 36 (4 weeks) and (b) for 894 m on Carbowax, 20M in FIGS. 37 (0 weeks), 38 (2 weeks), 39 (3 weeks) and 40 (4 weeks).

Figure 41:
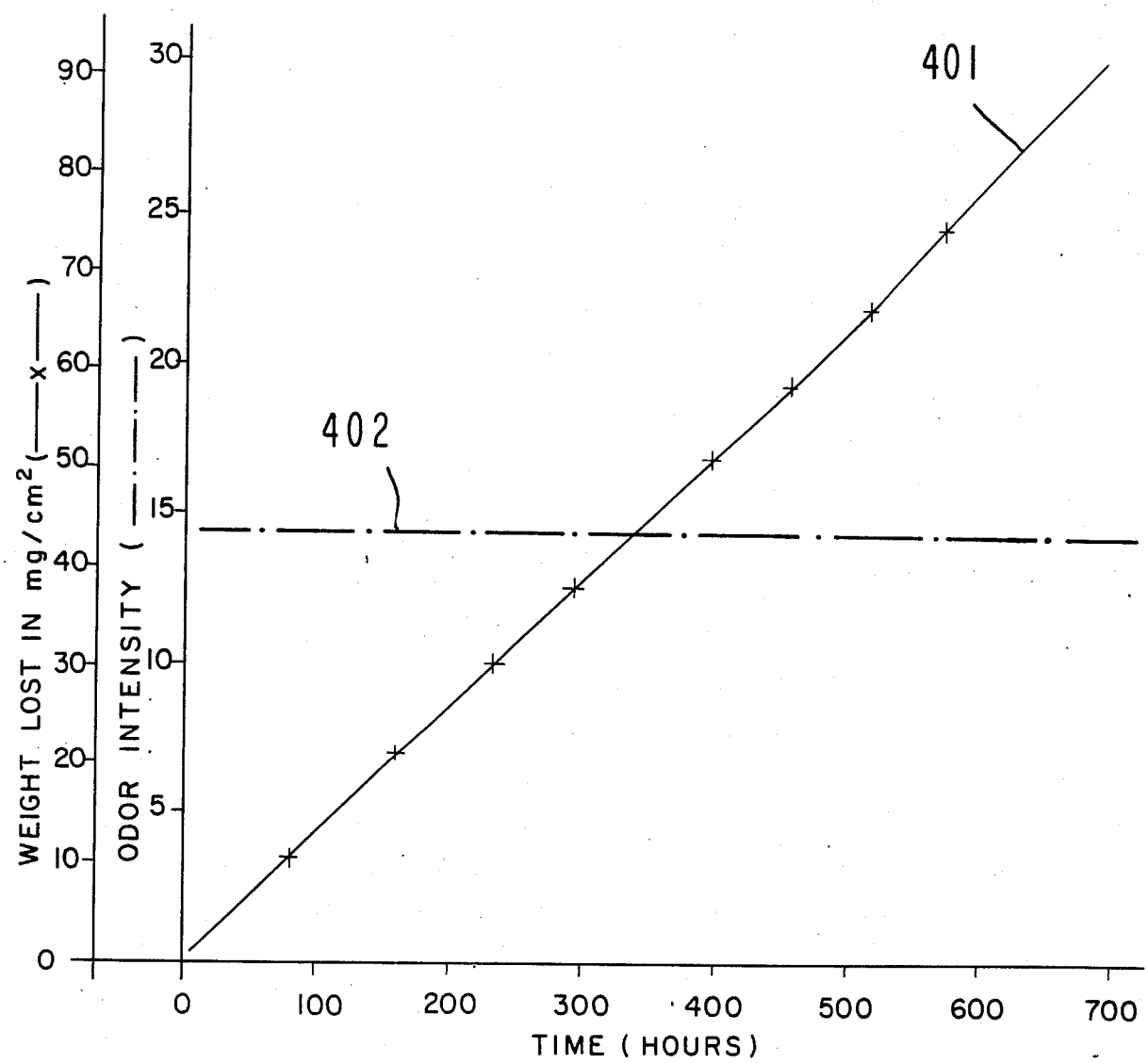
FIG. 41 is a dual graph for perfume composition "278 m"; the graph indicated by reference numeral "401" showing weight lost over a period of time as measured in mg/cm$^2$ and the line indicated by reference numeral "402" indicating odor intensity vs. time (showing essentially no change in odor intensity) where odor intensity is on a scale of 0–30 odor intensity units.

FIG. 41 sets forth a dual graph of weight loss vs. time for 278 m (as shown by the graph indicated by reference numeral "401") and for odor intensity on a scale of 0 to 30 units as shown by the graph indicated by reference numeral "402".

Discussion

The isolates were subjected to internal standard capillary GLC to conform sensory evaluations. In comparing the GLC results across the 4 week period, it is obvious that there is no apparent disproportionation of the fragrance over the 4 week exposure.

What is claimed is:

1. A hollow totally enclosed structure capable of the release into the space surrounding said structure at a substantially constant rate of at least one volatile material consisting of volatile material molecules, said volatile material being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans; said structure comprising:
   (i) a first thin finite hemi-ellipsoidal shell having a first single continuous circumference; and
   (ii) a second thin finite hemi-elliposoidal shell having a second single continuous circumference totally abutting and in continuous intimate contact with said first single continuous circumference, said first thin shell and said second thin shell totally enclosing an inner void with at least a first finite section of said first thin shell being a microporous polymer shell section consisting of a porous membrane having (i) the properties of transporting water vapor at a rate of between about 50 up to about 1000 g/m²/day at about 25° C. and at about 50% relative humidity at about atmospheric pressure and having an air transport rate of 100–20,000 Gurley seconds; and (ii) a thickness in the range of from about 0.01 mils up to about 20 mils, the said second thin shell having a porosity equal to or less than the porosity of said first finite thin shell, said porous polymer shell section having a porosity such that when said hollow totally enclosed structure is located in an ambient environment at a pressure of less than or equal to about one atmosphere at a point in time substantially immediately or subsequent to the commencement of functional operation of said structure and thereafter, in a controllable time release manner and at a constant rate, said volatile material molecules are transported at a constant mass flow rate both of the individual volatile components and totally, either:
   (i) onto the inner surface of said porous polymer shell section via an adsorption mechanism and from the outer surface of said porous polymer shell section to the atmosphere surrounding said structure via a desorption mechanism; and
   (ii) through said porous polymer shell section by means of capillary action,
   said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section.

2. The hollow totally enclosed structure of claim 1 wherein the polyolefin in the microporous polymer shell section is polypropylene; the thickness of the microporous polymer shell section is about 100 micrometers; the pore size of the microporous polymer shell section is approximately 0.1 micrometers; the void volume of the polypropylene is approximately 34 cubic centimeters per gram; and the density of the polypropylene is approximately 900 kilograms per cubic meter.

3. A structure comprising (a) a first hollow totally enclosed structure defined according to claim 1 and enclosing said first structure, (b) a second air-tight totally enclosed structure, said first totally enclosed structure having a volume less than said second air-tight totally enclosed structure, said first totally enclosed structure being of such dimensions that it is (i) enclosable within said second air-tight totally enclosed hollow structure, and (ii) the internal volume of said second air-tight totally enclosed hollow structure is greater than the external volume of said first hollow totally enclosed structure.

4. A hollow totally enclosed structure capable of controllable functional operation for the controlled release into the environment surrounding said structure of at least one consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans, comprising a thin shell, a section of which consists of a filled microporous polymer section, said thin shell totally enclosing an inner void, said thin shell having an inner surface and an outer surface, the inner surface thereof being the boundary of said inner void, said thin shell having a base portion and an upper portion, said base portion having an inner surface:

(a) contained totally within the inner void of said thin shell and in place on said inner surface of said base portion, a volatile composition existing in the liquid state at ambient conditions temporarily entrapped and totally entrapped in an entrapment material at least at the instant in time of commencement of functional operation of said structure, said volatile composition being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functions in humans;

(b) at least a finite section of said thin shell consisting of a filled microporous polymer shell section having an inner surface, said porous thin shell section consisting essentially of (i) a porous polymer lamina and (ii) in random admixture with said polymer lamina a filler dispersed in the pores of said polymer lamina, said filler being in the solid phase, the filler being in a phase separate from the polymer phase of the polymeric lamina; and (c) a non-porous containment means removably enclosing said filled porous polymer section and located outwardly from the said outer surface of said filled porous polymer shell section, the removal of said non-porous containment means causing the commencement of functional operation of said structure and the presence of said non-porous containment means preventing said functional operation when said non-porous containment means encloses said filled porous polymer section on its outer surface said filled porous polymer shell section having a porosity such that when said hollow totally enclosed structure is located in the ambient environment at a pressure of less than or equal to about one atmosphere at a point in time substantially immediately or subsequent to the commencement of functional operation of said structure and thereafter in a controllable time release manner, said volatile material molecules are transported at a substantially constant mass flow rate, both of the individual volatile components and totally, either:

(i) onto the inner surface of said filled porous polymer shell section via an adsorption mechanism and from the outer surface of said filled porous polymer shell section to the atmosphere surrounding said structure via a desorption mechanism, the said adsorption mechanism and the said desorption mechanism being operable as a result of the critical surface tension of said filler phase being greater than the critical surface tension of said volatile composition existing in the liquid state; or (ii) through said filled porous polymer shell section by means of capillary action, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section.

5. The hollow totally enclosed structure of claim 4 wherein said filled porous polymer shell section has a porosity such that when said hollow totally enclosed structure is located in an inert gas at a temperature of less than or equal to about one atmosphere at a point in time substantially immediately and subsequent to the commencement of functional operation of said structure and thereafter in a controllable time release manner, said volatile material molecules are transported at a substantially constant mass flow rate, both of the individual volatile components and totally onto the inner surface of said filled porous polymer shell section via an adsorption mechanism and from the outer surface of said filled porous polymer shell section to the atmosphere surrounding said structure via a desorption mechanism, the said adsorption mechanism and the said desorption mechanism being operable as a result of the critical surface tension of said filler phase being greater than the critical surface tension of said volatile composition existing in the liquid state.

6. A structure defined according to claim 4 wherein (i) said base portion comprises a first thin polymer shell having a curved surface and an inner void portion and an inner surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the said first circumferential edge thereof to said upper portion at the said second circumferential edge thereof.

7. A plurality of hollow totally enclosed structures laterally and detachably interconnected having a common midplane, each of said structure being defined individually according to claim 6, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.

8. A process for providing an environment with a consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functions in humans comprising the steps of:

(i) providing a hollow totally enclosed structure capable of controllable functional release into the environment surrounding said structure of at least one consumable material selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans, comprising a thin shell, a section of which consists of a filled microporous polymer section, said thin shell totally enclosing an inner void, said thin shell having an inner surface and an outer surface, the inner surface thereof being the boundary of said inner void, said thin shell having a base portion and an upper portion, said base portion having an inner surface:

(a) contained totally within the inner void of said thin shell and in place on said inner surface of said base portion, a volatile composition existing in the liquid state at ambient conditions temporarily entrapped and totally entrapped in an entrapment material at least at the instant in time of commencement of functional operation of said structure, said volatile composition being selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functions in humans;

(b) at least a finite section of said thin shell consisting of a filled microporous polymer shell section having an inner surface, said porous thin shell section consisting essentially of (i) a porous polymer lamina and (ii) in random admixture with said polymer lamina a filler dispersed in the pores of said polymer lamina, said filler being in the solid phase, the filler being in a phase separate from the polymer phase of the polymeric lamina; and (c) a non-porous containment means removably enclosing said filled porous polymer section and located outwardly from the said outer surface of said filled porous polymer shell section, the removal of said non-porous containment means causing the commencement of functional operation of said structure and the presence of said non-porous containment means preventing said functional operation when said non-porous containment means encloses said filled porous polymer section on its outer surface said filled porous polymer shell section having a porosity such that when said hollow totally enclosed structure is located in the ambient environment at a pressure of less than or equal to about one atmosphere at a point in time substantially immediately or subsequent to the commencement of functional operation of said structure and thereafter in a controllable time release manner, said volatile material molecules are transported at a substantially constant mass flow rate, both of the individual volatile components and totally, either:

(i) onto the inner surface of said filled porous polymer shell section via an adsorption mechanism and from the outer surface of said filled porous polymer shell section to the atmosphere surrounding said structure via a desorption mechanism, the said adsorption mechanism and the said desorption mechanism being operable as a result of the critical surface tension of said filler phase being greater than the critical surface tension of said volatile composition existing in the liquid state; or (ii) through said filled porous polymer shell section by means of capillary action, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section;

(i) placing said hollow totally enclosed structure in said environment;

(ii) removing the non-porous containment means enclosing said filled porous polymeric section from the said filled porous polymeric section; and (iii) permitting the resulting system to equilibrate.

9. A process for controllably dispensing continuously or discontinuously for discrete periods of time a volatile composition of matter selected from the group consisting of perfume compositions, herbicide compositions, insecticide compositions, animal repellent compositions, air freshener compositions, pheromone compositions, odor maskant compositions, deodorant compositions, insect repellent compositions and compositions for the evaluation of olfactory functioning in humans from a container into the environment surrounding said container which process comprises the steps of:

(a) entrapping the volatile composition of matter in an entrapment agent whereby a temporarily entrapped volatile composition is formed;

(b) providing a first thin shell section composed of a thin polymer shell having a curved surface and having an inner void portion, an inner surface and an outer surface and having a first continuous sealable circumferential outer edge and a first geometric configuration;

(c) placing the entrapped volatile composition in the inner void portion of said first thin shell section and onto the inner surface of said first thin shell section, said volatile composition being selected from the group consisting of perfume compositions, herbicide compositions, insecticide compositions, animal repellant compositions, air freshener compositions, pheremone compositions, odor maskant compositions, deodorant compositions for the evaluation of olfactory functions in humans and insect repellent compositions;

(d) providing a second thin shell section having a second sealable circumferential edge and having a shape and volume which are such that when said second shell is placed in conforming adjacent edgewise contact with said first shell, a totally enclosed shell structure is produced with said entrapped volatile composition being totally enclosed within said shell section;

(e) placing said second thin shell section having said second sealable circumferential continuous edge which substantially conforms in shape to said first sealable circumferential edge onto said first thin shell section whereby said first sealable edge is in closely fitting sealable proximity with said second circumferential edge; and (f) sealing said first sealable edge to said second sealable edge whereby the resulting shell structure enclosing said entrapped volatile composition is totally enclosed and substantially air-tight with the exception of ingress and egress of volatile composition molecules controllably and at a constant velocity through the polymer wall during functional operation of the resulting shell structure;

at least a finite section of said first thin shell section or said second thin shell section comprising a microporous polymer having a porosity such that when said hollow totally enclosed structure thus formed is located in the ambient environment at a pressure of less than or equal to about one atmosphere, said volatile material molecules are transported at a substantially constant mass flow rate, both of the individual volatile components and totally, onto the inner surface of said microporous polymer section via an adsorption mechanism and from the outer surface of said microporous polymer section via a desorption mechanism, said microporous polymer consisting essentially of polyolefin intimately admixed with a powder having an average particle diameter of from about 0.3 up to about 500 microms, said powder being a filler material in compatible with said polymer, said powder being in a proportion of about 5 to 100 parts by weight per 100 parts by weight of polymer, the said volatile composition having a volatility at ambient conditions which is higher than the transmissibility of said microporous polymer.

10. The process of claim 9 wherein the first thin shell section is composed of a non-porous and transparent polymer and said second thin shell section is a microporous polymeric membrane and is opaque at least at the instant in time of commencement of the functional operation of said structure, said microporous polymer membrane containing solid particles having an average particle diameter of from about 0.1 up to about 20 micrometers.

11. The process of claim 9 comprising the additional step (g) of placing the resulting shell structure when not in use into an outer all-enclosing container which outer container is non-porous and is composed of a material which prevents the volatile material molecules from being transported or diffusing therethrough, the dimensions of the outer container being such that the volume of said outer container and the shape of said outer container are such that the outer container totally encloses the inner container, said outer container having a sealable entrance therein whereby the shell structure defined according to claim 9 may be placed into and removed from said outer container and whereby said outer container may be sealed in an air-tight manner after the placing of said shell structure of claim 9 into said outer container.

12. The process of claim 9 wherein the volatile composition of matter entrapped in the entrapment agent is placed in a plurality of hollow totally enclosed structures which are laterally and detachably interconnected having a common midplane.

* * * * *